US009861547B2

(12) United States Patent
Crunick et al.

(10) Patent No.: US 9,861,547 B2
(45) Date of Patent: Jan. 9, 2018

(54) SYSTEMS AND METHODS FOR PREVENTING, MANAGING AND/OR TREATING PERIPHERAL NEUROPATHY, PERIPHERAL VASCULAR DISEASE, ERECTILE DYSFUNCTION, URINARY INCONTINENCE, CELLULITE AND OTHER CONDITIONS

(75) Inventors: John Crunick, Cranberry Township, PA (US); Tamas Becse, Wexford, PA (US); Louis L. Laskey, Jr., Prospect, PA (US); James S. Sergi, San Rafael, CA (US)

(73) Assignee: Sigma Instruments Holdings, LLC, Cranberry Township, PA (US)

( * ) Notice: Subject to any disclaimer, the term of this patent is extended or adjusted under 35 U.S.C. 154(b) by 938 days.

(21) Appl. No.: 14/344,311

(22) PCT Filed: Sep. 14, 2012

(86) PCT No.: PCT/US2012/055538
§ 371 (c)(1),
(2), (4) Date: Nov. 20, 2014

(87) PCT Pub. No.: WO2013/040432
PCT Pub. Date: Mar. 21, 2013

(65) Prior Publication Data
US 2015/0126914 A1    May 7, 2015

Related U.S. Application Data

(60) Provisional application No. 61/616,974, filed on Mar. 28, 2012, provisional application No. 61/535,225, filed on Sep. 15, 2011.

(51) Int. Cl.
*A61H 1/00* (2006.01)
*A61N 1/36* (2006.01)

(52) U.S. Cl.
CPC ......... *A61H 1/008* (2013.01); *A61N 1/36003* (2013.01); *A61N 1/36014* (2013.01)

(58) Field of Classification Search
CPC ............ A61N 1/36003; A61N 1/36007; A61N 1/36014; A61N 1/3603; A61N 1/36031;
(Continued)

(56) References Cited

U.S. PATENT DOCUMENTS 3,499,437 A    3/1970   Balamuth
4,530,360 A    7/1985   Duarte
(Continued)

FOREIGN PATENT DOCUMENTS

DE    10306795 A1    9/2004
KR    10-0400870 B   10/2003
(Continued)

OTHER PUBLICATIONS

Chinese Office Action (English), 201480039884.X, dated Aug. 10, 2016.
(Continued)

*Primary Examiner* — Justine Yu
*Assistant Examiner* — Kathrynn Lyddane
(74) *Attorney, Agent, or Firm* — Polsinelli PC

(57) ABSTRACT

Systems and methods for preventing, managing and/or treating peripheral neuropathy and peripheral vascular disease in a patient. The systems and methods include measuring, optimizing transmissibility and coordinating the delivery of pressure (e.g., sound) waves that are delivered using higher frequency RF band energy in a pulsed manner to carry the energy to larger areas of the patient's tissue. The pressure wave may be delivered at generally the same time a heart pulse beat of the patient is detected.

11 Claims, 29 Drawing Sheets

(58) Field of Classification Search
CPC .......... A61N 1/36034; A61N 1/40; A61N 2007/0078; A61N 2007/0082; A61N 7/00; A61H 1/008; A61H 23/003; A61H 23/006; A61H 23/02; A61H 23/0218; A61H 23/0245

See application file for complete search history.

(56) References Cited

U.S. PATENT DOCUMENTS

| | | | |
|---|---|---|---|
| 4,946,692 | A | 8/1990 | Bernhardt et al. |
| 4,984,127 | A | 1/1991 | Evans |
| 5,209,221 | A | 5/1993 | Riedlinger |
| 5,300,095 | A | 4/1994 | Salazar |
| 5,413,550 | A | 5/1995 | Castel |
| 5,586,067 | A | 12/1996 | Gross |
| 5,601,526 | A | 2/1997 | Chapelon et al. |
| 6,321,119 | B1 | 11/2001 | Kronberg |
| 6,413,230 | B1 | 7/2002 | Haupt et al. |
| 6,419,648 | B1 | 7/2002 | Vitek et al. |
| 6,514,220 | B2 | 2/2003 | Melton, Sr. et al. |
| 6,539,328 | B1 | 3/2003 | Cremonese et al. |
| 6,540,700 | B1 | 4/2003 | Fujimoto et al. |
| 6,565,520 | B1 | 5/2003 | Young |
| 6,645,162 | B2 | 11/2003 | Friedman et al. |
| 7,123,967 | B2 | 10/2006 | Weinberg |
| 7,144,417 | B2 | 12/2006 | Colloca et al. |
| 7,435,232 | B2 | 10/2008 | Liebschner |
| 7,519,427 | B2 | 4/2009 | Sakagami et al. |
| 7,894,907 | B2 | 2/2011 | Cowan et al. |
| 7,899,542 | B2 * | 3/2011 | Cowan .............. A61N 1/37217 607/46 |
| 8,048,006 | B2 | 11/2011 | Harris |
| D711,900 | S | 8/2014 | Crunick et al. |
| 9,314,190 | B1 * | 4/2016 | Giuffrida ................ A61B 5/11 |
| 9,517,349 | B2 | 12/2016 | Becse et al. |
| 2002/0099409 | A1 * | 7/2002 | Hui .................... A61G 7/05776 606/201 |
| 2003/0125649 | A1 | 7/2003 | McIntosh et al. |
| 2004/0015106 | A1 * | 1/2004 | Coleman ............ A61H 23/0236 601/3 |
| 2004/0171970 | A1 | 9/2004 | Schleuniger et al. |
| 2005/0043659 | A1 | 2/2005 | Challis et al. |
| 2005/0222524 | A1 | 10/2005 | Fielding et al. |
| 2006/0009810 | A1 | 1/2006 | Mann et al. |
| 2006/0122579 | A1 | 6/2006 | Pisciottano |
| 2006/0160158 | A1 | 7/2006 | Ebright |
| 2006/0184075 | A1 | 8/2006 | Restle et al. |
| 2007/0073361 | A1 | 3/2007 | Goren et al. |
| 2007/0091091 | A1 | 4/2007 | Gardiner et al. |
| 2007/0173903 | A1 | 7/2007 | Goren et al. |
| 2007/0203533 | A1 | 8/2007 | Goren et al. |
| 2008/0021353 | A1 | 1/2008 | Menzi et al. |
| 2008/0077434 | A1 | 3/2008 | Man et al. |
| 2008/0183164 | A1 | 7/2008 | Elkins |
| 2009/0018404 | A1 | 1/2009 | Fendelander et al. |
| 2009/0043293 | A1 * | 2/2009 | Pankratov .............. A61N 1/328 606/9 |
| 2009/0149782 | A1 | 6/2009 | Cohen |
| 2009/0178626 | A1 | 7/2009 | Greeson |
| 2009/0326607 | A1 | 12/2009 | Castel et al. |
| 2010/0094187 | A1 | 4/2010 | Murinson |
| 2010/0105933 | A1 | 4/2010 | Chen et al. |
| 2010/0131025 | A1 | 5/2010 | Henry |
| 2011/0118810 | A1 | 5/2011 | Cowan et al. |
| 2011/0166621 | A1 | 7/2011 | Cowan et al. |
| 2011/0171325 | A1 | 7/2011 | Lozano |
| 2011/0213253 | A1 | 9/2011 | Kruglick |
| 2014/0031866 | A1 | 1/2014 | Fuhr |
| 2014/0194790 | A1 | 7/2014 | Crunick et al. |
| 2015/0080990 | A1 | 3/2015 | Crunick et al. |
| 2016/0113840 | A1 | 4/2016 | Crunick et al. |
| 2016/0151238 | A1 | 6/2016 | Crunick et al. |

FOREIGN PATENT DOCUMENTS

| | | |
|---|---|---|
| KR | 10-2010-0082140 A | 7/2010 |
| WO | WO 99-34724 A2 | 7/1999 |
| WO | WO 02-098318 A2 | 12/2002 |
| WO | WO 2010/009141 A1 | 1/2010 |
| WO | WO 2011/080191 A1 | 7/2011 |
| WO | WO 2013/040443 A2 | 3/2013 |
| WO | WO 2013/040451 A2 | 3/2013 |

OTHER PUBLICATIONS

Extended European Search Report, EP14807934.6, dated Feb. 1, 2017.
Final Office Action, U.S. Appl. No. 14/372,989, dated May 2, 2016.
Final Office Action, U.S. Appl. No. 14/895,843, dated Oct. 17, 2016.
Non-Final Office Action, U.S. Appl. No. 14/895,843, dated Apr. 22, 2016.
Non-Final Office Action, U.S. Appl. No. 15/373,637, dated Apr. 26, 2017.
Notice of Allowance, U.S. Appl. No. 14/372,989, dated Aug. 10, 2016.
Response to Final Office Action, U.S. Appl. No. 14/372,989, dated Jul. 29, 2016.
Response to Non-Final Office Action, U.S. Appl. No. 14/895,843, dated Sep. 22, 2016.
Response to Restriction Requirement, U.S. Appl. No. 14/205,105, dated Mar. 1, 2017.
Restriction Requirement, U.S. Appl. No. 14/205,105, dated Dec. 1, 2016.
European Search Report, EP12832599.0, dated Apr. 2, 2015.
International Search Report and Written Opinion, PCT/US2014/040953, dated Oct. 6, 2014.
International Search Report and Written Opinion, PCT/US2012/055538, dated Jan. 30, 2013, 11 pages.
International Search Report and Written Opinion, PCT/US2012/055564, dated Feb. 28, 2013, 10 pages.
International Search Report and Written Opinion, PCT/US2013/021973, dated May 15, 2013, 15 pages.
International Search Report and Written Opinion, PCT/US2012/055551, dated Feb. 26, 2013, 12 pages.

* cited by examiner

SYSTEMS AND METHODS FOR PREVENTING, MANAGING AND/OR TREATING PERIPHERAL NEUROPATHY, PERIPHERAL VASCULAR DISEASE, ERECTILE DYSFUNCTION, URINARY INCONTINENCE, CELLULITE AND OTHER CONDITIONS

CROSS REFERENCE TO RELATED APPLICATIONS

The present application claims priority to U.S. Provisional Patent Application No. 61/535,225, which is entitled Systems and Methods for Preventing and/or Treating Peripheral Neuropathy and Peripheral Vascular Disease, and was filed Sep. 15, 2011.

This application also claims priority to U.S. Provisional Patent Application No. 61/616,974, filed Mar. 28, 2012, and entitled Systems and Methods for Preventing, Managing and/or Treating Peripheral Neuropathy, Peripheral Vascular Disease, Erectile Dysfunction, Urinary Incontinence, Cellulite and Other Conditions. The contents of all of the above-mentioned patent applications are hereby incorporated by reference in their entireties.

FIELD OF THE INVENTION

The present invention relates to medical devices and methods. More specifically, the present invention relates systems and methods for preventing and/or treating peripheral vascular and peripheral neuropathy secondary to diabetes mellitus or other diseases or medical conditions.

BACKGROUND OF THE INVENTION

Diabetes is a serious disease that can develop from lack of insulin production in the body or due to the inability of the body's insulin to perform its normal everyday functions. Insulin is a substance produced by the pancreas gland that helps process ingested food and turn it into energy.

Diabetes affects approximately 25.8 million Americans as per a 2011 NIH study. An estimated 285 million people, corresponding to 6.4% of the world's adult population, will live with diabetes in 2010. The number is expected to grow to 438 million by 2030, corresponding to 7.8% of the adult population according a recent WHO study. Diabetes is classified into 2 different types: Type 1 and Type 2. Type 1 is usually associated with juvenile diabetes and is often linked to heredity. Type 2, commonly referred to as adult onset diabetes, is characterized by elevated blood sugars, often in people who are overweight or have not attended to their diet properly.

Many complications can be associated with diabetes. Diabetes disrupts the vascular system, affecting many areas of the body such as the eyes, kidneys, legs, and feet. People with diabetes should pay special attention to their feet, as 25% of diabetic patients will develop foot problems related to the disease.

Diabetic foot conditions develop from a combination of causes including poor circulation and neuropathy. Diabetic neuropathy can cause insensitivity or a loss of ability to feel pain, heat, and cold. Diabetics suffering from neuropathy can develop minor cuts, scrapes, blisters, or pressure sores that they may not be aware of due to the insensitivity. If these minor injuries are left untreated, complications may result and lead to ulceration and possibly even amputation. Neuropathy can also cause deformities such as bunions, hammer toes, and Charcot feet.

Peripheral neuropathy can be brought about by diseases or conditions other than diabetes. Examples of such diseases or conditions include trauma (e.g., motor vehicle accidents, falls or sports injuries), prolonged pressure (e.g., using a cast or crutches), repetitive motions (e.g., typing), vitamin deficiencies (e.g., lacking in vitamins B-1, B-6, B-12, E and niacin), alcoholism, infections (e.g., certain viral or bacterial infections including Lyme disease, shingles (varicella-zoster), Epstein-Barr, hepatitis C and HIV/AIDS), autoimmune diseases (e.g., lupus, rheumatoid arthritis and Guillain-Barre syndrome), kidney disease, liver disease, underactive thyroid (hypothyroidism), inherited disorders (e.g., Charcot-Marie-Tooth disease and amyloid polyneuropathy), tumors, and exposure to poisons (e.g., toxic substances like heavy metals and certain medications like those used to treat cancer (chemotherapy)).

Diabetes often leads to peripheral vascular disease that inhibits a person's blood circulation. With this condition, there is a narrowing of the arteries that frequently leads to significantly decreased circulation in the lower part of the legs and the feet. Poor circulation contributes to diabetic foot problems by reducing the amount of oxygen and nutrition supplied to the skin and other tissue, causing injuries to heal poorly. Poor circulation can also lead to swelling and dryness of the foot. Preventing foot complications is more critical for the diabetic patient because poor circulation impairs the healing process and can lead to ulcers, infection, and other serious foot conditions.

Peripheral vascular disease can be brought about by diseases or conditions other than diabetes. Examples of such diseases or conditions include vasculitis (inflammation of the blood vessels, occurring either as a primary condition or associated with connective tissue diseases such as lupus), injuries to blood vessels (from accidents such as auto accidents or sports injuries), blood-clotting disorders, and damage to blood vessels during surgery.

The aforementioned vascular and neurological issues can lead to erectile dysfunction (ED) in males. ED can be defined as persistent failure to generate sufficient penile body pressure to achieve vaginal penetration and/or the inability to maintain this degree of penile rigidity until ejaculation. Erectile dysfunction is common among men of all ages, ethnicities, and cultural backgrounds. It has been recently estimated that more than 152 million men worldwide experienced ED in 1995, and that this number will rise by 170 million, to approximately 322 million by the year 2025. Although the exact prevalence of erectile dysfunction in the United States male population is not known, estimates have ranged from 12% of males above age 18 to 25-30% of men between ages 60 and 70.

There is a need in the art for systems, devices, and methods for preventing, managing and/or treating diabetic neuropathy and peripheral vascular disease and related conditions, such as, for example, ED.

BRIEF SUMMARY OF THE INVENTION

Disclosed herein are systems and methods for preventing, managing and/or treating peripheral neuropathy and peripheral vascular disease in a patient. In one embodiment, the systems and methods include measuring, optimizing transmissibility and coordinating the delivery of pressure (e.g., sound) waves that are delivered using higher frequency RF band energy in a pulsed manner to carry the energy to larger areas of the patient's tissue. In one embodiment, the pressure wave may be delivered at generally the same time a heart pulse beat of the patient is detected with the objective of stressing and/or stimulating the valves within the blood vessels. This aspect may be considered treatment directly of the circulatory system. Additionally, in one embodiment, pulsed frequency ranges from 1 Hz to 300 Hz may be used in both a sweep manner and static calculated frequencies within that range to stimulate neurological response. These frequencies have been determined to produce a neurological response.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 7 FIG. 5 is a schematic diagram of the system employing the selected treatment RF head and the EMG sensor for the embodiment of the system depicted in FIG. 4.

FIG. 10B-1 is a screen shot of the display of the system of FIG. 4, wherein the screen shot illustrates a manual pulse rate selection system for setting the parameters for a rectangle pulse output.

FIG. 10B-2 is a is a screen shot of the display of the system of FIG. 4, wherein the screen shot illustrates a scanned pulse rate selection system for setting the parameters for a rectangle pulse output.

FIG. 10C-1 is a screen shot of the display of the system of FIG. 4, wherein the screen shot illustrates a manual pulse rate selection system for setting the parameters for a modulated pulse output.

FIG. 10C-2 is a is a screen shot of the display of the system of FIG. 4, wherein the screen shot illustrates a scanned pulse rate selection system for setting the parameters for a modulated pulse output.

DETAILED DESCRIPTION

Figure 1:
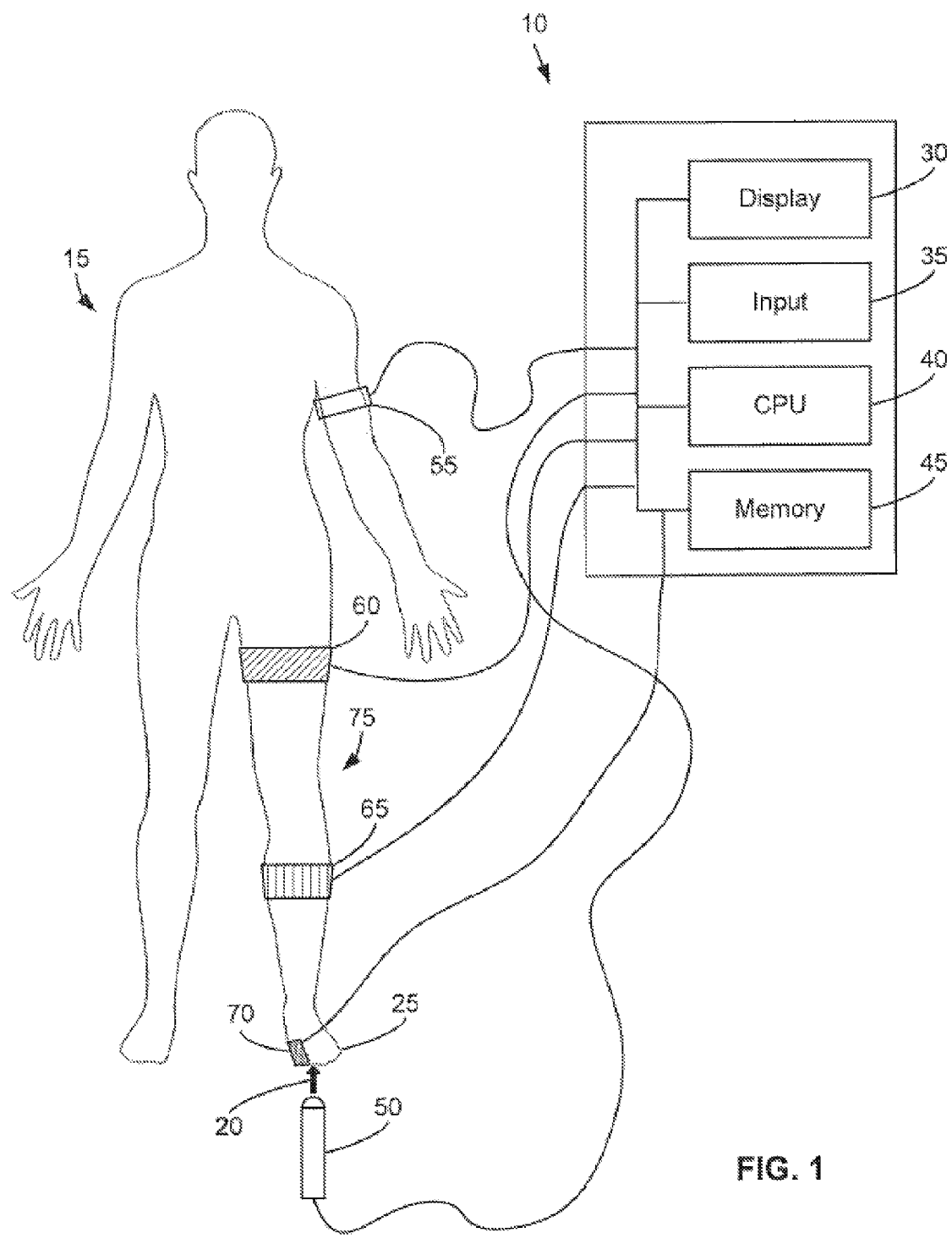
FIG. 1 is a schematic diagram of a system for preventing and/or treating diabetic neuropathy and peripheral vascular disease in a patient.

The present disclosure relates to medical devices and methods for preventing and/or treating peripheral neuropathy and peripheral vascular disease secondary to diabetes mellitus or other diseases or medical conditions.

Disclosed herein are systems 10 and methods 200 for preventing, managing and/or treating neuropathy and peripheral vascular disease in a patient 15. In one embodiment, the systems 10 and methods include coordinating the delivery of pressure waves (e.g., sound waves) 20 to a patient's tissue 25 such that the pressure wave is delivered at generally the same time a heart pulse beat of the patient is detected for circulatory stimulation or in pulses that range in frequency of 1 Hz to 300 Hz for neurological stimulation. In other words, in one embodiment, a burst of pressure wave energy 20 is delivered to the patient's target tissue 25 each time the patient's heart pulse beat is detected.

As can be understood from FIG. 1, which is a schematic diagram of the system 10 being used on the patient 15, the system includes a display 30, an input 35, a central processing unit (CPU) 40, a memory 45, a pressure wave (RF energy) generator (e.g., sound wave generator) 50, and a pulse monitoring device 55. The display may include a LCD or other type of screen for displaying information associated with the use of the system 10 in treating a patient 15. For example, the display 30 may display the patient's age, name, medical history, treatment durations, timing sequences, and protocols, pulse rates and heart performance graphs, and pressure wave shapes, frequencies, etc.

The input 35 is in electrical communication with the display 30 and may include a keyboard, touch screen, mouse, stylus, and/or other type of input mechanism. The input is configured to receive information associated with the treatment of the patient, such as patient age, tissue condition and location, desired treatment durations, timing sequences, and protocols, etc.

The CPU 40 is in electrical communication with the display 30, the input 35, and memory 45. The memory 45 may include treatment parameters and protocols associated with the treatment of the patient such as, for example, pressure wave types, frequencies, magnitude, etc. for different type of patients, patient tissue, and tissue conditions.

The pressure wave generating device 50 is in electrical communication with the CPU 40 and is configured to deliver a pressure wave (e.g., sound wave) to a tissue 25 of the patient 15, such as, for example, an extremity of the patient like the patient's foot, leg, hand or arm. The pressure wave generating device 50 may be in the form of a handheld wand, as shown, or may be equipped with a strap or other arrangement to allow the pressure wave generating device 50 to be strapped to the patient 15. The pressure wave generating device 50 may be capable of generating a wide range of pressure energy (e.g., sound energy) 20, including ultrapressure (e.g., ultrasound), and short waves through long waves. In one embodiment, the pressure energy 20 generated by the pressure wave generating device 50 is a long wave pressure wave.

Typically, a conductive gel is applied to the patient's tissue 25 to aid in the transmission of the pressure wave to the body part and the underlying tissues and muscle. The pressure wave generating device 50 is configured to deliver a pressure wave having a frequency between 500 kHz and 1000 kHz. In a preferred embodiment, the pressure wave generating device 50 delivers an 800 kHz pressure wave to the patient 15. Preferably, the pressure wave has sinusoidal waveform, although other waveforms and wave profiles may also be generated.

In various embodiments, the pressure wave generated by the pressure wave generating device 50 may be modulated to transmit the pressure wave throughout the tissue 25 and into adjacent body parts. For example, the pressure wave may be pulsed at a lower frequency. In one example, the pressure wave having a frequency between 500 kHz and 1000 kHz may be pulsed at lower frequency between 1 Hz and to 300 Hz to transmit the energy of a pressure wave in frequencies known to evoke neurological potentials. The pulsing of the wave also reduces heat build up in the tissues and is intended to maximize the mechanical influence of the lower frequencies on the tissues and/or nerves.

The pulse monitoring device 55 is in communication with the CPU and configured to detect a pulse of the patient 15. The pulse monitoring device 55 may be configured for coupling to a patient's arm, finger, chest or etc. The pulse monitoring device 55 may be in the form of an EKG machine, echocardiography machine, blood pressure detecting device (e.g., blood pressure cuff), etc.

Direct circulatory stimulation may be coordinated directly with the heartbeat. For example, in one embodiment, the CPU 40 causes the pressure wave generating device 50 to generate a pressure wave of a desired frequency, magnitude, and duration at a desired time relative to a heart beat of the patient 15 as detected by the pulse monitoring device 55. For example, in one embodiment, the pressure wave may be generated at generally the same time as the pulse of the patient. In another embodiment, the pressure wave may be generated continuously from a time just prior to the pulse of the patient to a time just after the pulse of the patient. In yet another embodiment, the pressure wave may be generated upon a pulse being detected by the pulse monitoring device, the generation of the pressure wave ceasing upon the end of the detected pulse. In yet another embodiment, the pressure wave may be generated at desired time period after a pulse is first being detected by the pulse monitoring device and continue for another time desired time period.

Figure 10A:
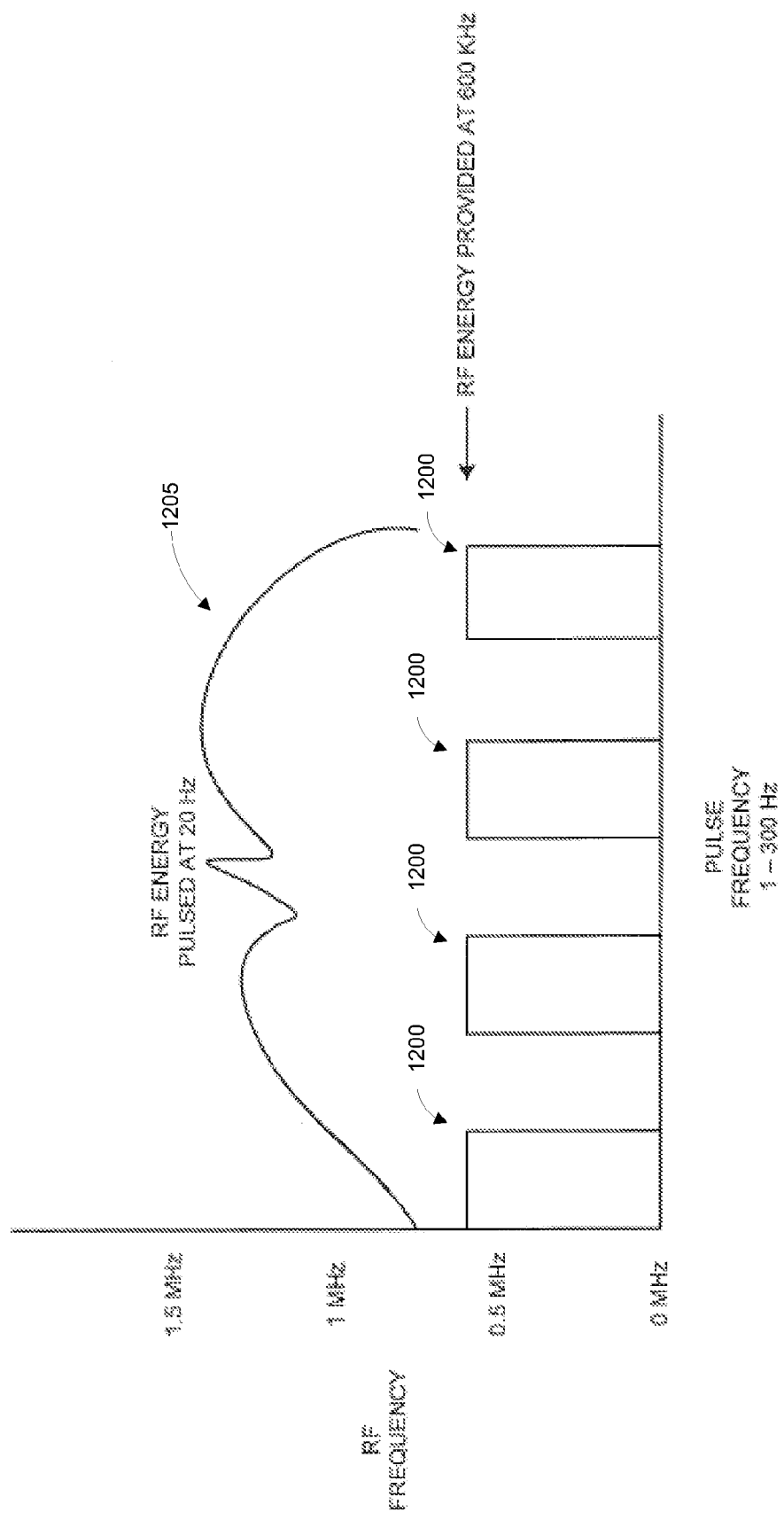
FIG. 10A is a graph of RF energy being administered at an example identified (optimum) RF frequency and pulsed at an example identified (optimum) pulse frequency.
Figure 10B:
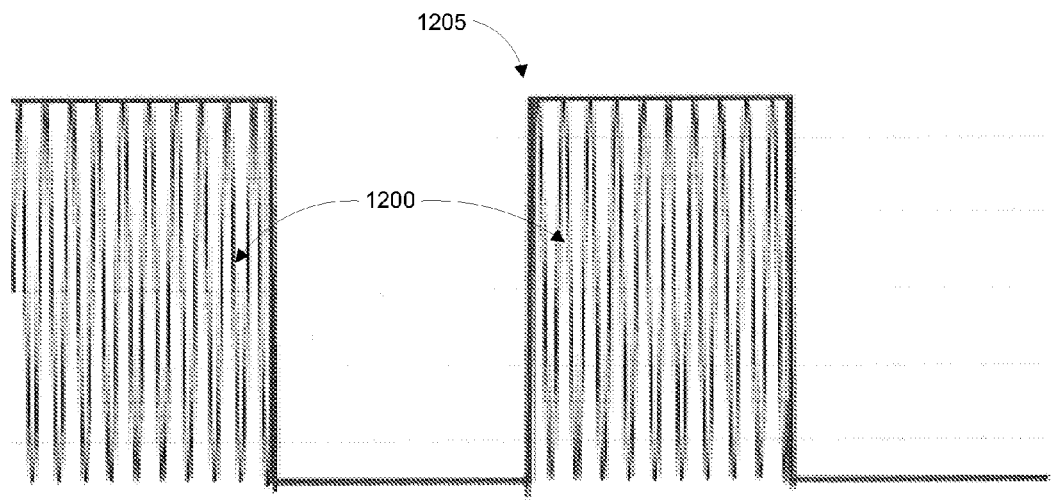
FIG. 10B is an example of a pulsed output signal similar to that depicted in FIG. 10A.

Neurological stimulation need not be coordinated directly with the heartbeat. For example, in one embodiment, the CPU 40 causes the pressure wave-generating device 50 to generate a pressure wave of a desired frequency, magnitude, and duration. For example, the pressure wave is achieved by introducing a pulsed pressure wave by pulsing an 800 MHz transmission wave in the frequency range of 1 Hz to 300 Hz in a sweep pattern so as to introduce all frequencies within the range within a programmable time period, as can be understood from FIG. 10B-1. The pressure wave may be generated continuously and modulated. FIG. 10B illustrates two types of patterns including amplitude modulation. While a square wave is shown in FIG. 10B-1, sinusoidal waves may also be used in one embodiment of the device.

As indicated in FIG. 1, in various embodiments, the system 10 also includes an electrical stimulation device 60, a temperature sensor 65, and an oxygen sensor 70 that are in electrical communication with at least one of the display 30, the input 35, the CPU 40, and memory 45.

Figure 2:
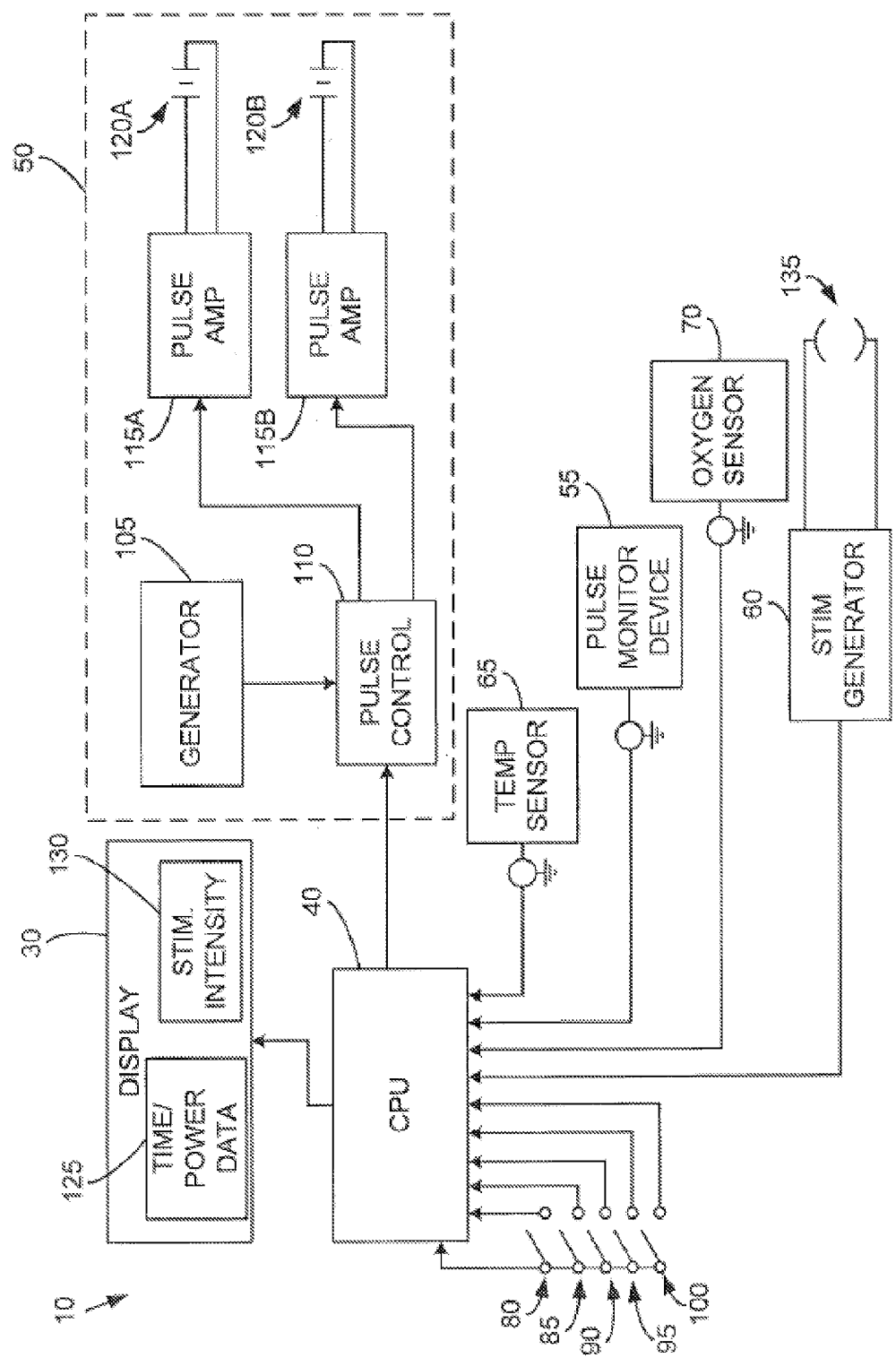
FIG. 2 is a schematic diagram illustrating one embodiment of the system disclosed herein

The electrical stimulation device 60 is configured to deliver one or more electrical pulses to a limb 75 adjacent to the tissue 25 being treated. As shown, the electrical stimulation device 60 is placed on the thigh of the limb 75 (e.g. leg) that is attached to the tissue 25 being treated. The electrical pulses cause one or more muscles of the limb 75 to contract and thereby increase the flow of blood throughout the limb, including blood flowing to the tissue and additionally aiding in lymphatic drainage 25. In one embodiment, the electrical stimulation device 60 includes one or more electrodes 135, as shown in FIG. 2, which engage the skin of the patient 15 and deliver the electrical pulses to the limb 75.

The electrical stimulation device 60 may be wearable such that it may be attached to the patient 15. The wearable electrical stimulation device 60 may be attached to the patient 15 by an adhesive or may be placed circumferentially around a portion of the patient, such as the limb 75. As shown, the electrical stimulation device 60 may be positioned around the left thigh of the patient 15 receiving treatment in the left foot.

As indicated in FIG. 1, the temperature sensor 65 is positioned on the patient to gather temperature data and may be used to assess the effectiveness of the treatment. The temperature sensor 65 is preferably positioned an equal distance from the electrical stimulation device 60 and the location of the pressure wave administration; however in other embodiments, the temperature sensor 65 may be position near or adjacent to the electrical stimulation device 60 or the tissue 25 being treated. In the embodiment shown in FIG. 1, the temperature sensor 65 is position to gather temperature data from the calf muscle to monitor the effectiveness of the treatment.

The temperature sensor 65 may be wearable such that it may be attached to the patient 15. The wearable temperature sensor 65 may be attached to the patient 15 by an adhesive or may be placed circumferentially around a portion of the patient, such as the limb 75. As shown, the temperature sensor 65 may be positioned around the left calf of the patient 15 receiving treatment in the left foot.

The oxygen sensor 70 measures the oxygen saturation of the patient's blood 15. In one embodiment, the oxygen sensor 70 is configured to measure the oxygen levels in blood flowing through a particular location. As shown in FIG. 1, the oxygen sensor 70 may be positioned on an extreme digit (e.g., toe) of the limb 75 to monitor oxygen levels in the limb. In various embodiments, the oxygen sensor 70 may be any pulse oximeter, which is a commonly device in the medical field. As such, the oxygen sensor 70 may also measure the heart rate or pulse at the extreme digit. The pulse data gathered by the oxygen sensor 70 may be used in conjunction with the pulse data gathered by the pulse monitor 55 to modify the treatment as desired.

FIG. 2 is a diagram illustrating another embodiment of the system 10. As shown, the CPU 40 is in electrical communication with the display 30, the pressure wave generating device 50, the temperature sensor 65, the pulse monitor device 55, the oxygen sensor 70, and the electrical stimulation device 60. The CPU 40 may also be in communication with plurality of switches 80-100 that may be opened or closed to control the operation of various aspects of the system 10.

By way of example and not limitation, a first switch 80 may be closed to start the treatment procedure. Similarly, a second switch 85 may be manipulated to power up or power down the system 10 and its various components such as the pressure generating device 50 and the electrical stimulation device 60. A third switch 90 may be used to control the duration of the treatment procedure, while a fourth switch 95 may be used to alternate between a single output and the interference output for modulating the pressure wave of the pressure wave generating device 50. A fifth switch 100 may be used to control the intensity of the stimulation provided by the electrical stimulation device 60. In other embodiments, a greater number or a fewer number of switches may be used.

FIG. 2 also depicts one embodiment of the pressure wave generating device 50. As shown, one embodiment of the pressure wave generating device 50 includes a pressure generator 105 that is configured to generate a pressure wave having a frequency of 800 kHz+/−200 kHz and a pulse modulator 110 configured to generate modulation pulses having frequencies between 1 to 300 Hz to modulate the pressure wave. The pressure wave or the modulated wave is then received at one or more pulse amplifiers 115A and 115B. The amplified signals are then received at one or more transducers 120A and 120B where the electrical signal is converted to sonic and/or ultrasonic waves.

Prior to, during, or after a treatment conducted using the system 10, the display 30 may display time and power data 125 for the procedure. The display 30 may also display data 130 related to the stimulation intensity provided by the electrical stimulation device 60 through the electrodes 135.

Various embodiments of the system 10 may contain more or less features according to the intended use and/or user of the system. For example, one embodiment of the system 10 may be configured for home use by a patient. This embodiment of the system 10 may not have extensive monitoring equipment, such as the temperature sensor 65, the pulse monitor device 55, or the oxygen sensor 70. Conversely, another embodiment of the system 10 may be provided for clinical use. A clinical embodiment of the system 10 may include all of the monitoring devices described herein, as well as other monitoring equipment or medical devices as desired by a medical professional.

Figure 3:
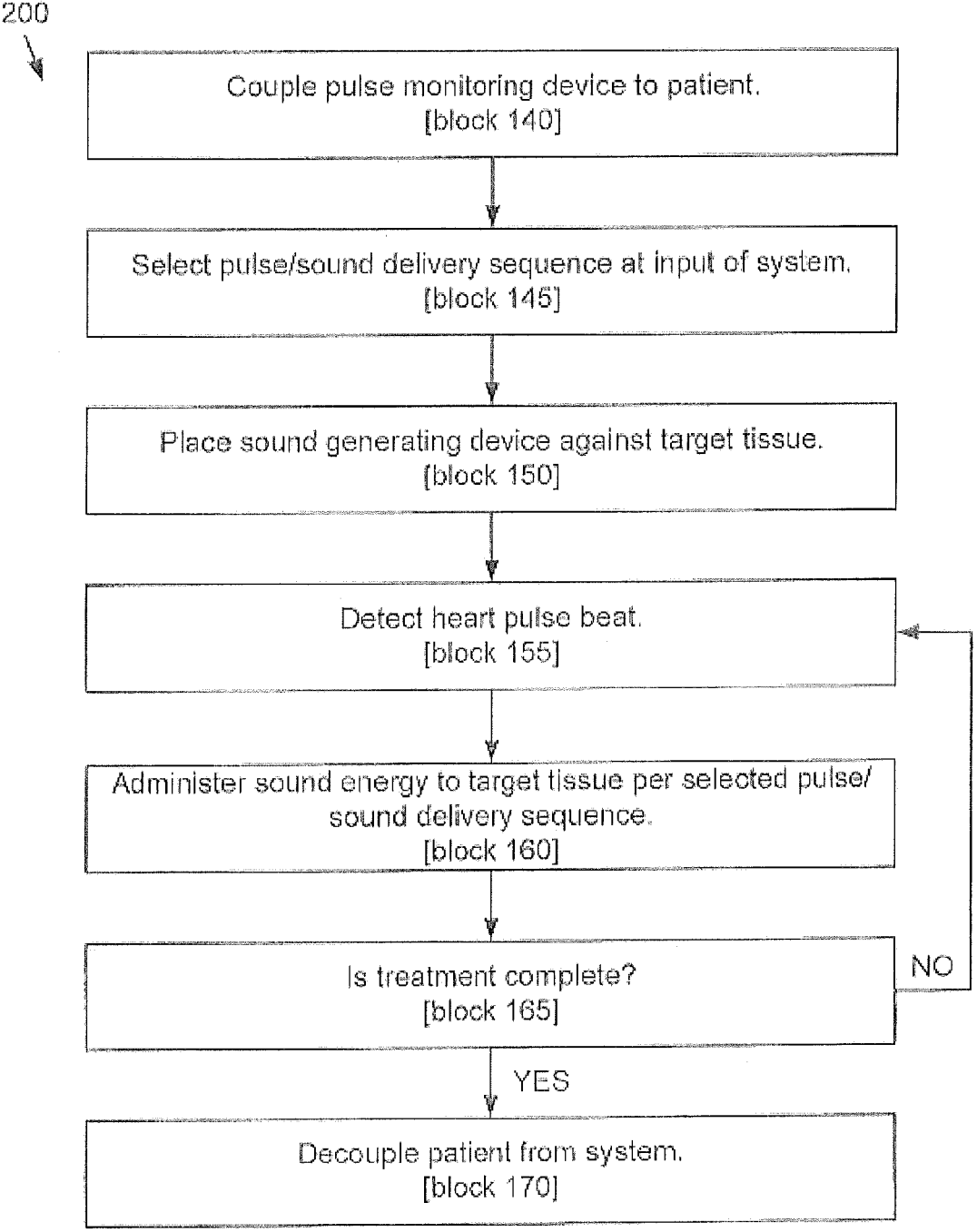
FIG. 3 is a flow chart illustrating one embodiment of the method disclosed herein.

As indicated in FIG. 3, which is a flow chart illustrating one embodiment of the method disclosed herein, the pulse monitoring device 55 is coupled to the patient [block 140]. A desired pulse/pressure delivery sequence is selected for the system via the input [block 145]. For example, the pressure energy could be selected to be long wave pressure energy and delivered with each detected pulse over the duration of a detected pulse.

The pressure generating device 50 is placed against the target tissue 25 of the patient 15 [block 150]. The system 10 is activated to deliver the treatment, wherein the heart pulse beat is detected [block 155] and, for each (or every other or some other selected sequence) detected heart pulse beat (Circulatory) or sweeping pulsed frequencies (Neurological), pressure energy is delivered to the target tissue per the selected pulse/pressure delivery sequence [block 160]. The delivery sequence repeats through blocks 155-160 until the treatment is complete [block 165]. The patient can then be decoupled from the system [block 170].

Depending on the embodiment, electrical stimulation of the muscles of the patient's limb (e.g., in the context of a patient's leg, the hamstring and/or quadriceps muscles) is delivered to the limb muscles via the electrical stimulation device 60. The delivered electrical stimulation may be coordinated with the pulse rate detection and/or delivery of the pressure waves or introduced independently of those variables. For example, the electrical stimulation could be delivered just prior to the delivery of the pressure wave, just subsequent to the delivery of the pressure wave, at the same time as the delivery of the pressure wave, etc.

The system and method disclosed herein is advantageous in that it stimulates the nervous system and circulatory system to prevent and/or treat or treating peripheral neuropathy and peripheral vascular disease.

In one embodiment, the system and method disclosed herein may include administering RF energy to patient tissue at a RF frequency determined to have the highest transmissibility in the tissue and at a pulse frequency determined to result in the highest electromyogram reading. As a result, the administration of the RF energy occurs at a RF frequency that will cause the RF energy to travel the greatest distance through the patient tissue, and the administration of the RF energy will be tailored to provide the most beneficial nerve stimulation.

Figure 4:
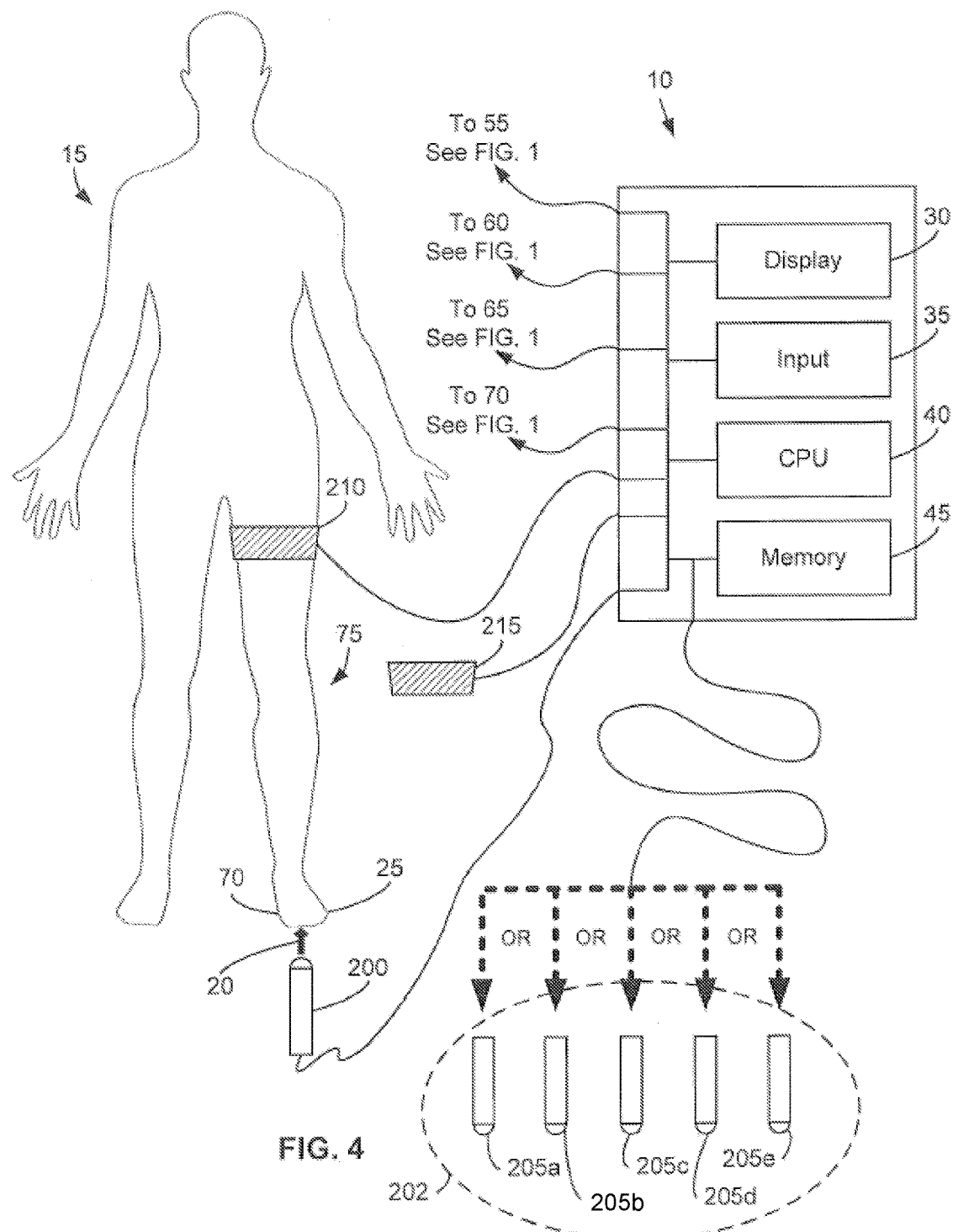
FIG. 4 is a schematic diagram of an alternative embodiment of the system being used on the patient.

As can be understood from FIG. 4, which is a schematic diagram of the system 10 being used on the patient 15, the system 10 of FIG. 4 may be generally the same as the system 10 depicted in FIG. 4. For example, the system 10 of FIG. 4 includes a display 30, an input 35, a central processing unit (CPU) 40, a memory 45, a pressure wave (RF energy) generator 50, a pulse monitoring device 55, an electrical stimulation device 60, a temperature sensor 65, and an oxygen sensor 70. Each of these components may be in electrical communication with each other as described above and, further, may be configured to have the features and operate as described above.

However, unlike the embodiment depicted in FIG. 1, the embodiment of the system 10 depicted in FIG. 4 may further include an evaluation RF head 200, a plurality 202 of treatment RF heads 205a-g, a RF antenna 210, and an EMG sensor 215. The evaluation RF head 200 and RF antenna and/or and acoustic measuring device 210 are capable of being placed in electrical communication with the CPU 40.

Figure 5:
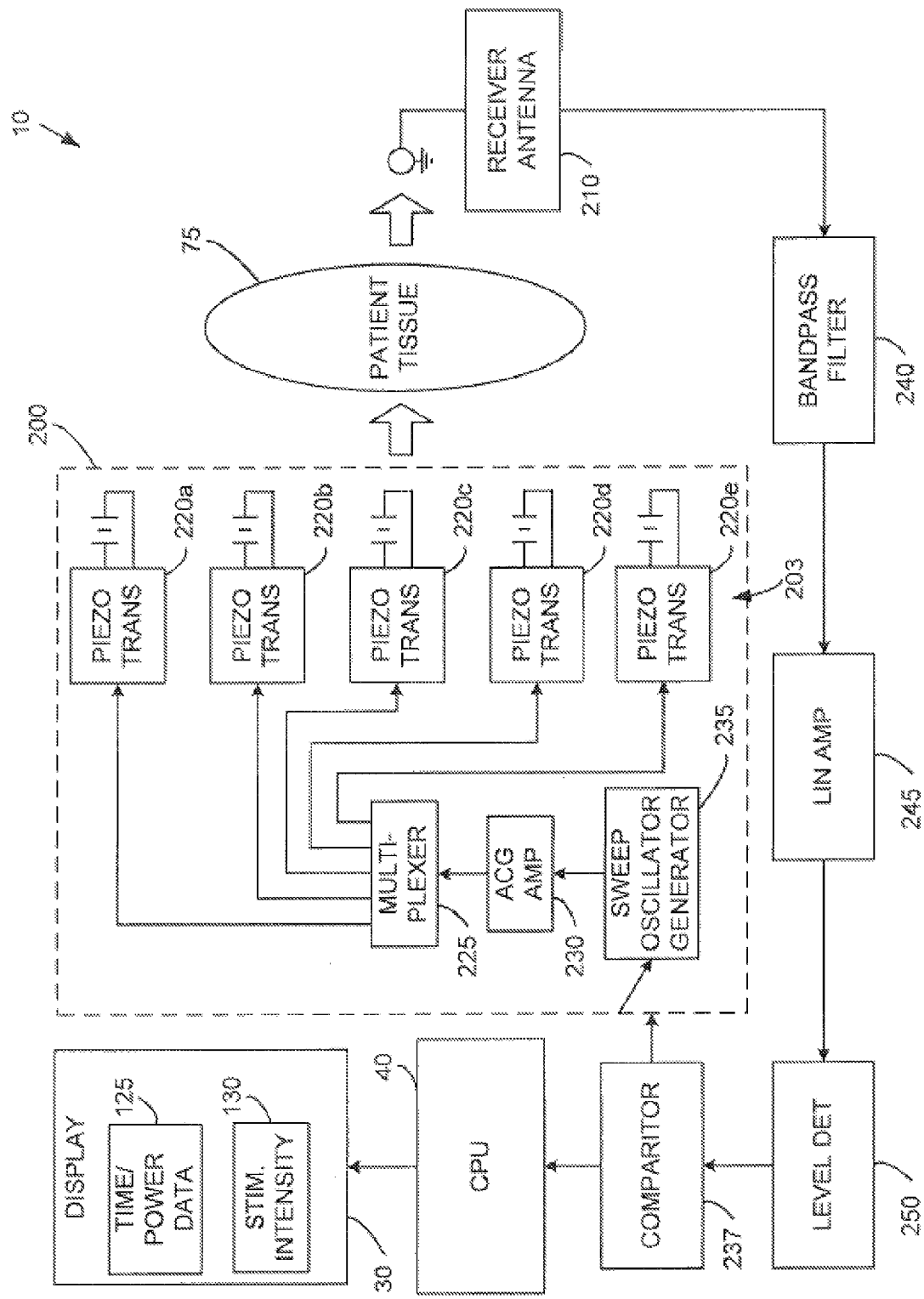
FIG. 5 is a schematic diagram of the system employing the evaluation RF head and the RF antenna for the embodiment of the system depicted in FIG. 4.

As illustrated in FIG. 5, which is a schematic diagram of the system 10 employing the evaluation RF head 200 and the RF antenna 210, the evaluation RF head 200 includes an array 203 of piezoelectric transducers 220a-e electrically coupled to a multi-plexer or pulse control 225 that is electrically coupled to an automatic gain control amplifier 230 electrically coupled to a sweep oscillator generator 235. The evaluation RF head 200 is electrically coupled to a comparator 237 that is electrically coupled to the CPU 40 and display 30 described above with respect to FIG. 2.

Each piezoelectric transducer 220a-e of the array 203 is individually tuned to generate RF energy at a distinct frequency as compared to the other piezoelectric transducers of the array. The piezoelectric transducers 220a-e forming the array 203 of the evaluation RF head 200 provide a range of distinct RF energy frequencies over a range of between approximately 500 KHz and approximately 1.5 MHz at steps of between approximately 50 KHz and approximately 200 KHz. For example, a first piezoelectric transducer 220a may be tuned to 500 KHz, the second piezoelectric transducer 220b may be tuned to 600 KHz, and so forth through the rest of the piezoelectric transducers such that the array 203 is capable of providing RF energy at a frequency range of between approximately 500 KHz and 1.5 MHz with steps of 100 KHz, resulting in an array 203 having 11 individually tuned piezoelectric transducers. Thus, the array 203 is configured to generate RF energy over a range of frequencies not possible via a single piezoelectric transducer.

As can be understood from FIG. 5, the RF receiver antenna 210 is electrically coupled to a bandpass filter 240 that is electrically coupled to a linear amplifier 245 electrically coupled to a level detector 250 electrically coupled to the comparator 237. As indicated in FIGS. 4 and 5, the evaluation RF head 200 is applied to patient tissue of a patient limb or other patient structure 75, and the RF receiver antenna and or acoustic measuring device 210 is applied to the limb or other structure 75 at a different location spaced apart from the location wherein the head 200 is being applied to the patient tissue. The RF receiver antenna is configured to detect RF energy transmitted through the patient limb 75 from the evaluation RF head 200.

When the evaluation RF head 200 and RF receiver antenna 210 are applied to the patient limb 75, the system 10 is configured to cause the evaluation RF head 200 to administer RF energy to the patient limb 75 over a range of RF frequencies by the sweep oscillator generator 235 generating a series of frequencies in a step fashion across the range of frequencies of the array 203 and the multi-plexer 225 sending the appropriate stepped frequency to the appropriate piezoelectric transducer 120a-120e when said appropriate stepped frequency is generated by the oscillator generator 235. As the array 203 of the head 200 sweeps through the various frequencies, the RF receiver antenna 210 senses the administered RF energy transmitted through the patient. The comparator 237, in conjunction with the CPU 40, identifies which RF frequency of the range of RF frequencies administered to the patient via the array 203 of the head 200 has the most transmissitivity through the patient. The system 10, via, for example, the display 30, recommends a treatment RF head from the plurality of treatment RF heads 202a-2302e that is capable of providing the identified RF frequency.

Each treatment RF head 205a-205e of the plurality 202 treatment RF heads shown in FIG. 4 has a piezoelectric transducer tuned to a unique frequency different from those of the other heads 205a-205e. Thus, the plurality 202 of treatment heads 205a-205e may be made up of a sufficient variety of treatment RF heads so as to cover a range of RF frequencies in a stepped fashion. For example, treatment RF head 205a-205e of the plurality 202 is individually tuned to generate RF energy at a distinct frequency as compared to the other heads 205a-205e of the plurality 202. The heads 205a-205e of the plurality 202 provide a range of distinct RF energy frequencies over a range of between approximately 500 KHz and approximately 1.5 MHz at steps of between approximately 50 KHz and approximately 200 KHz. For example, the first treatment RF head 205a may have a piezoelectric transducer tuned to 500 KHz, the second treatment RF head 205b may have a piezoelectric transducer 220b may be tuned to 600 KHz, and so forth through the rest of the treatment RF heads such that the plurality 202 of treatment heads 205a-205e is capable of providing RF energy at a frequency range of between approximately 500 KHz and 1.5 MHz with steps of 100 KHz, resulting in plurality 202 having 11 individually tuned treatment RF heads. Thus, a treatment RF head 205a-205e can be selected from the plurality 202 to match the RF frequency identified via the array 203 and comparator 237 as discussed above with respect to FIG. 4.

Figure 6:
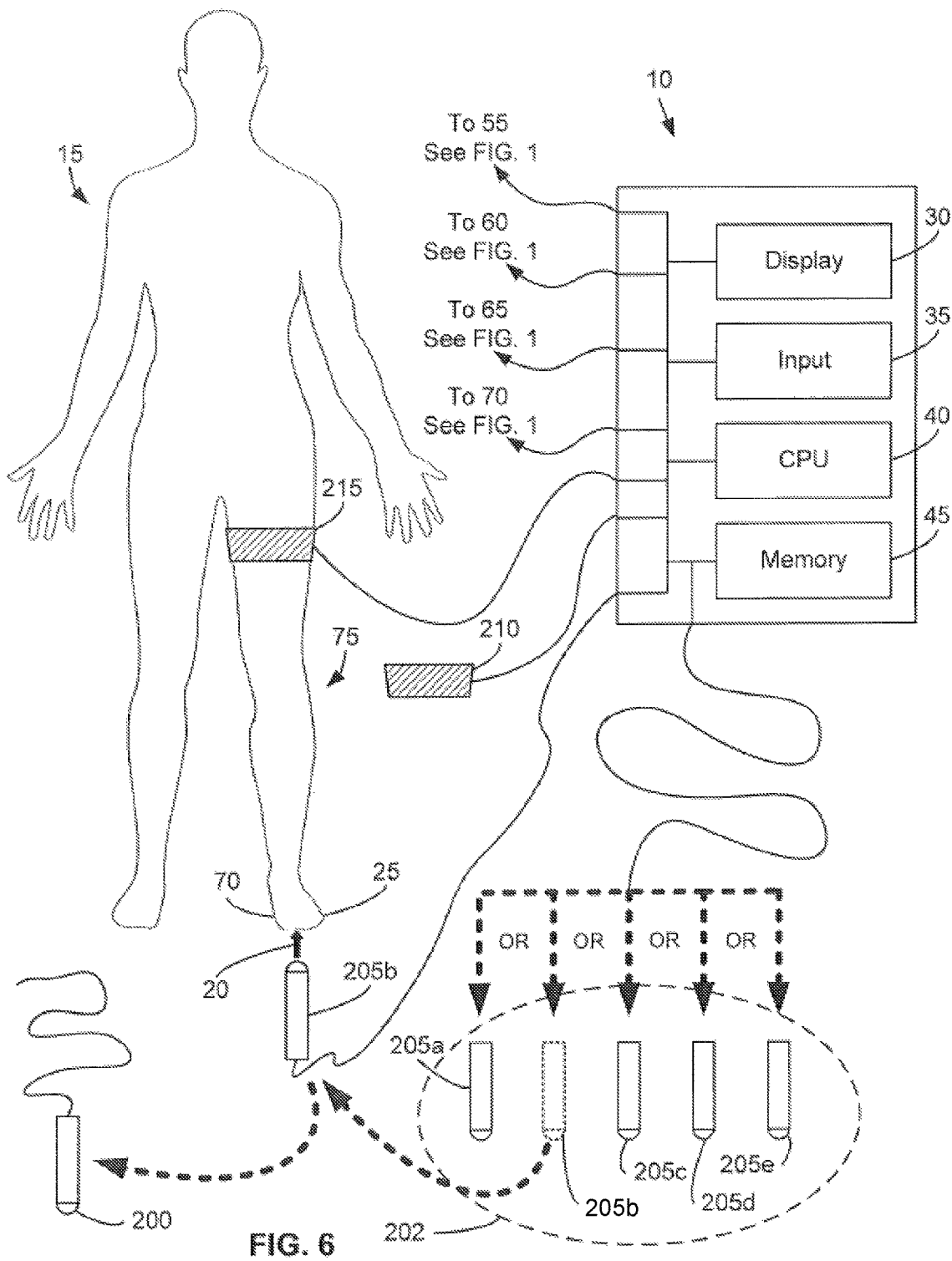
FIG. 6 is a schematic diagram of the system embodiment of FIG. 4, wherein the selected treatment RF head and EMG sensor are coupled to the system and being applied to the patient.

Once a treatment RF head 205a-205e is selected from the plurality 202 that matches the identified RF frequency, the selected RF treatment head is electrically coupled to the system 10, as illustrated in FIG. 6. For example, by using the array 203 and comparator 237 as described above with respect to FIG. 4, it is determined that a frequency of 600 KHz has the greatest transmissibility through the patient limb 75 and, as a result, the system 10 recommends from the plurality 202 of heads the treatment RF head 205b, which is tuned to operate at 600 KHz. As shown in FIG. 6, the treatment RF head 205b is electrically coupled to the system 10, and the EMG sensor 215 is electrically coupled to the system 10. The treatment RF head 205b and EMG sensor 215 are both applied to the patient limb 75.

Figure 7:
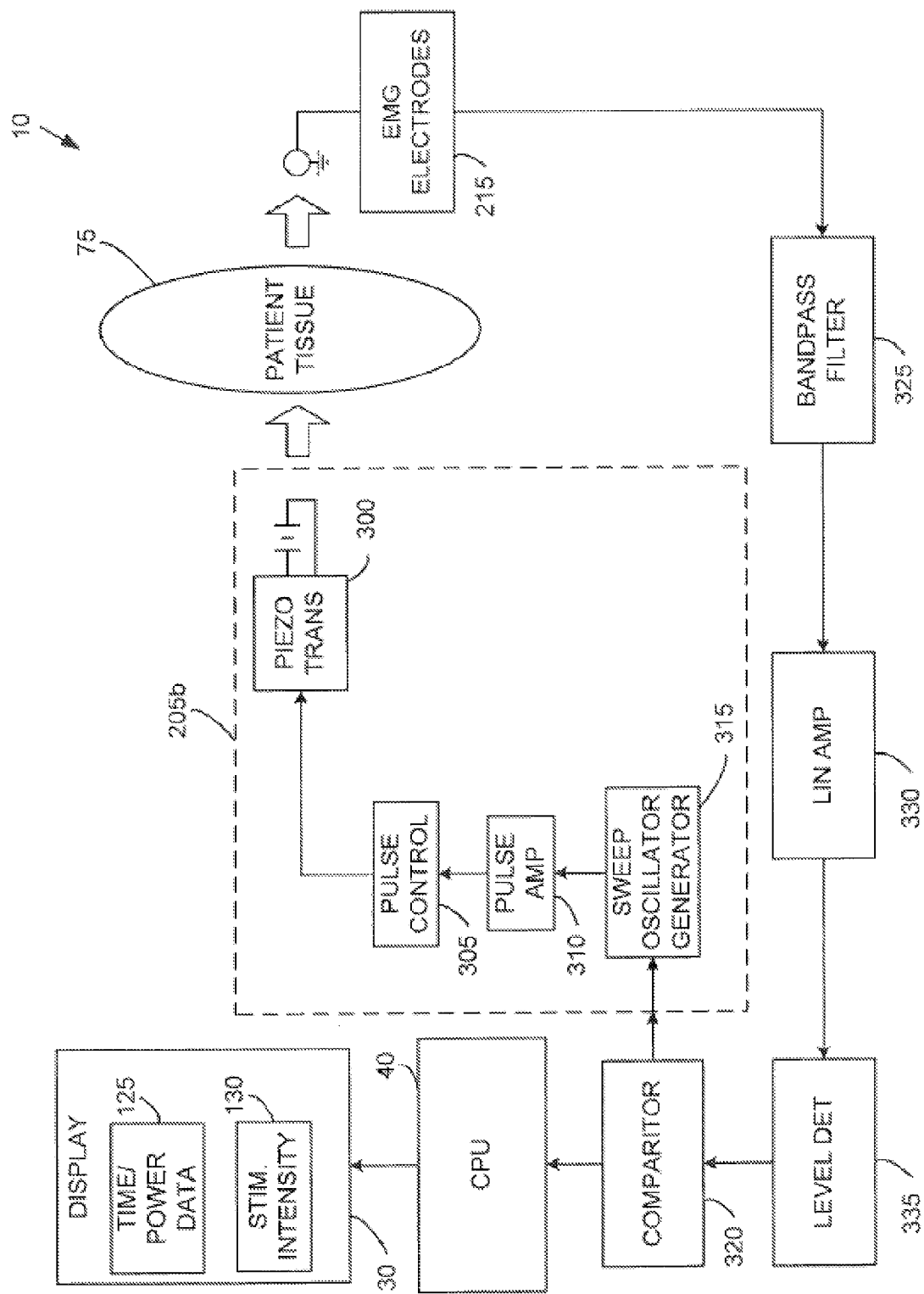

The system 10 now appears as schematically depicted in FIG. 7. Specifically, the selected treatment RF head 205b includes piezoelectric transducer 300 electrically coupled to a pulse control 305 that is electrically coupled to a pulse amplifier 310 electrically coupled to a sweep oscillator generator 315. The treatment RF head 205b is electrically coupled to a comparator 320 that is electrically coupled to the CPU 40 and display 30 described above with respect to FIG. 2.

As can be understood from FIG. 7, the EMG sensor 215, which has electrodes, is electrically coupled to a bandpass filter 325 that is electrically coupled to a linear amplifier 330 electrically coupled to a level detector 335 electrically coupled to a comparator 320. As indicated in FIGS. 6 and 7, the treatment RF head 205b is applied to patient tissue of a patient limb or other patient structure 75, and the EMG sensor 215 is applied to the limb or other structure 75 at a different location spaced apart from the location wherein the head 205b is being applied to the patient tissue. The EMG sensor is configured to detect electromyogram in the patient limb 75 from resulting from RF energy administered to the patient limb via the treatment RF head 205b.

When the treatment RF head 205b and EMG sensor 215 are applied to the patient limb 75, the system 10 is configured to cause the treatment RF head 205b to administer RF energy to the patient limb 75 at the identified RF frequency (which is 600 KHz in this example) over a range of pulse frequencies by the sweep oscillator generator 315 and pulse control 305 causing the administered 600 KHz RF energy to pulse at a series of frequencies in a step fashion across a range of pulse frequencies generated by the oscillator generator 315. In one embodiment, the generator 315 is configured to cause the treatment RF head 205b to administer RF energy at the identified RF frequency (which is 600 KHz in this example) to the patient over a range of pulse frequencies between approximately 1 Hz and approximately 300 Hz at steps that are defined in the software via an algorithm that allows the user to determine the scan time, in one embodiment, between approximately 1 Hz and approximately 30 Hz. Optimum scan times are established for each tissue type and/or body region in a database from empirical data. For example, a database contained in the memory of the system can be used to pre-select scan times based on the tissue or area of concern entered into the interface of the system, each tissue type or area of concern being correlated in the data base to specific scan times.

Figure 10C:
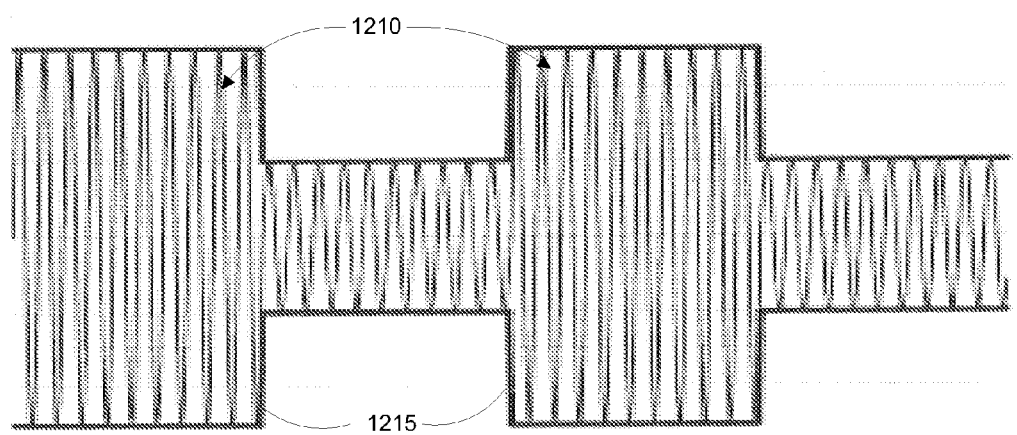
FIG. 10C is an example of a modulated output signal.
Figures 1, 10B:
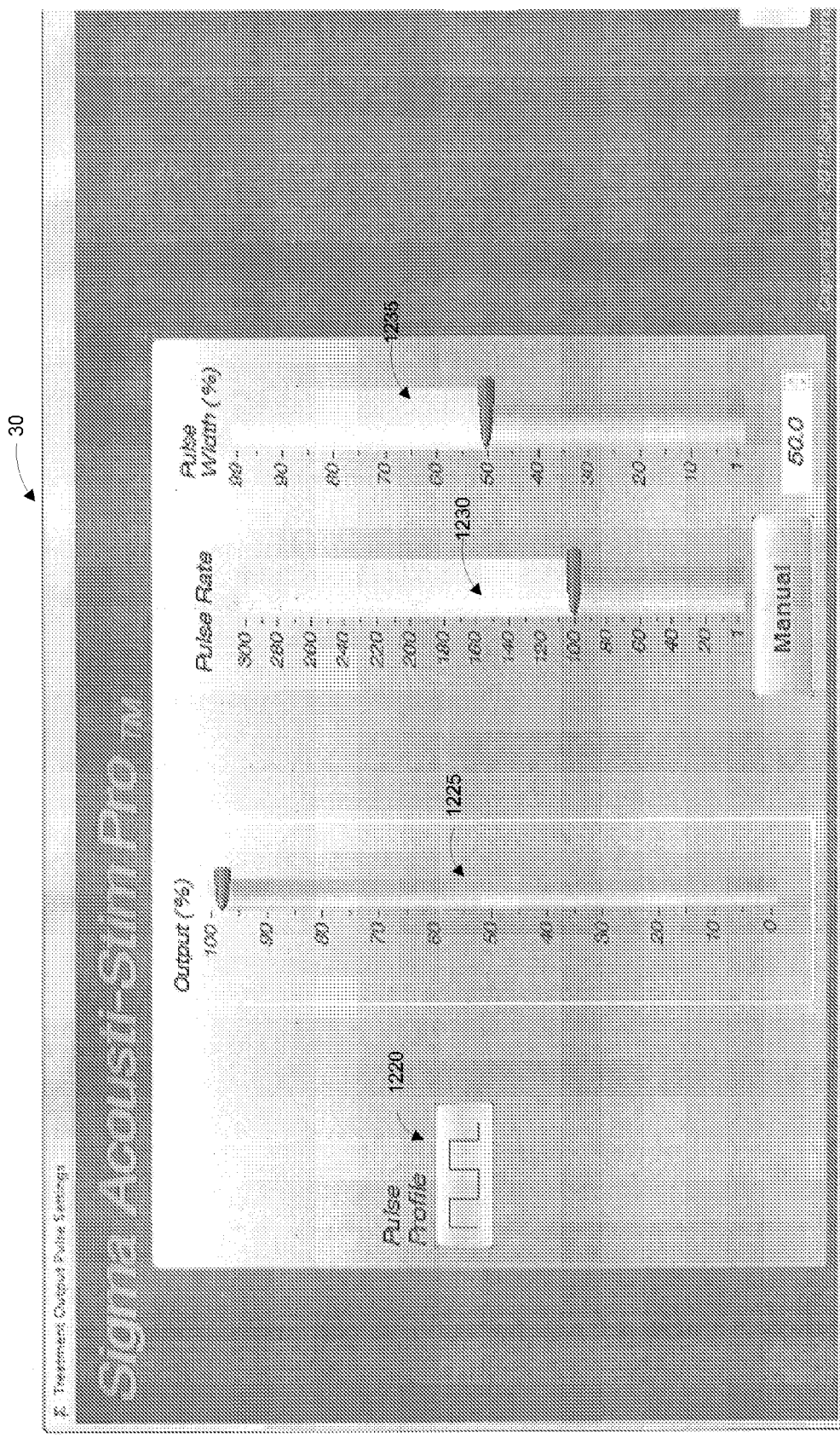
Figures 2, 10B:
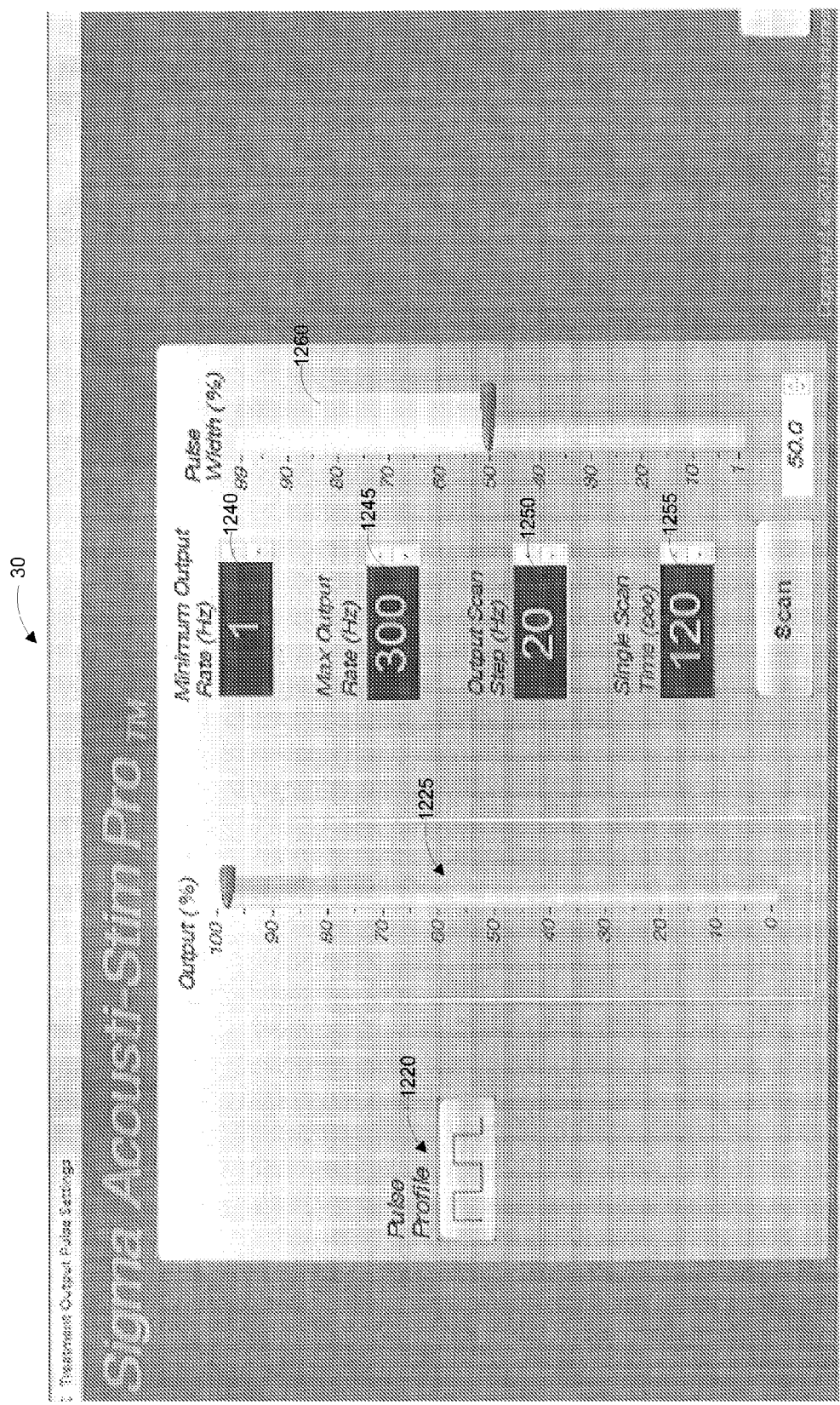
Figures 1, 10C:
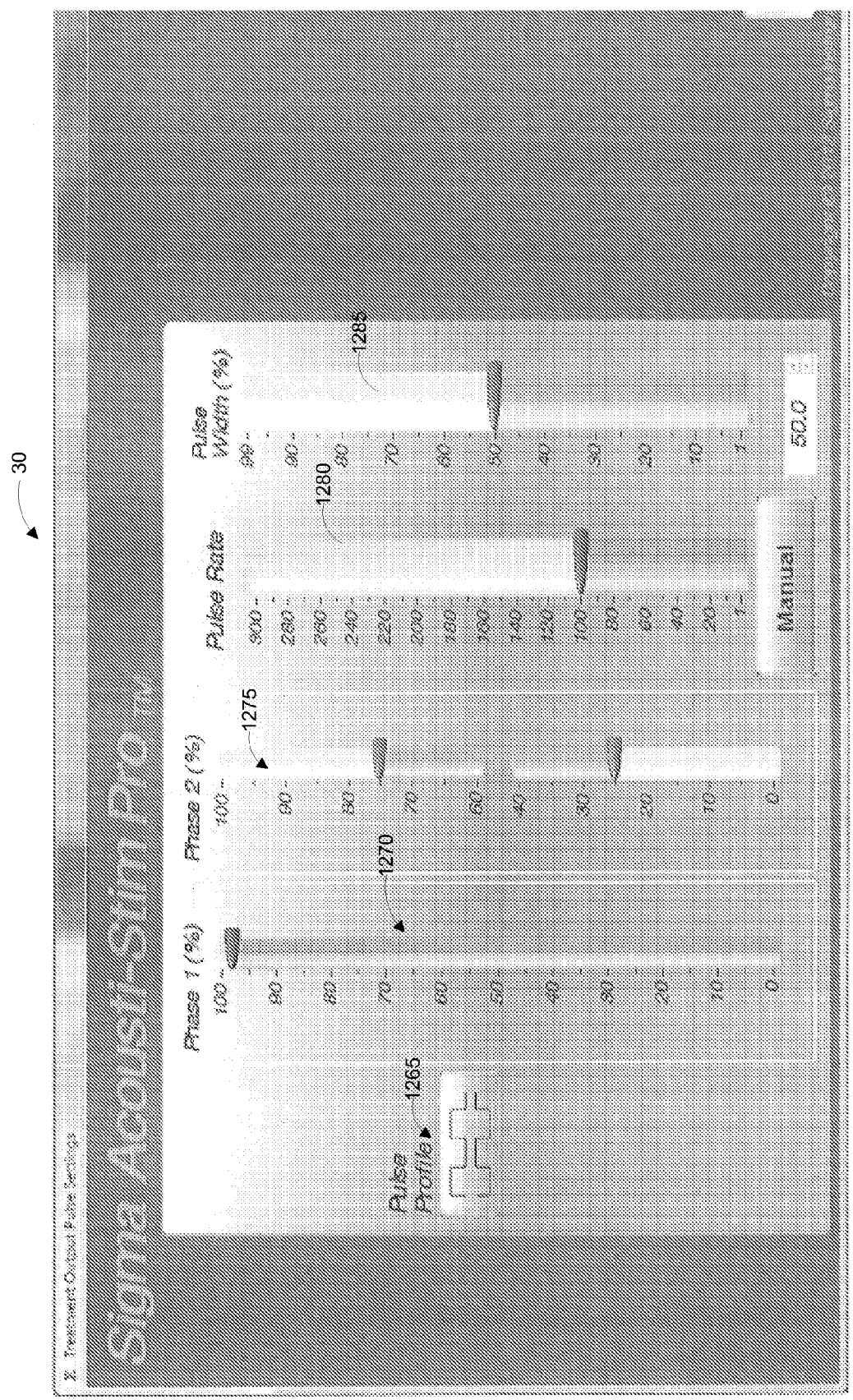
Figures 2, 10C:
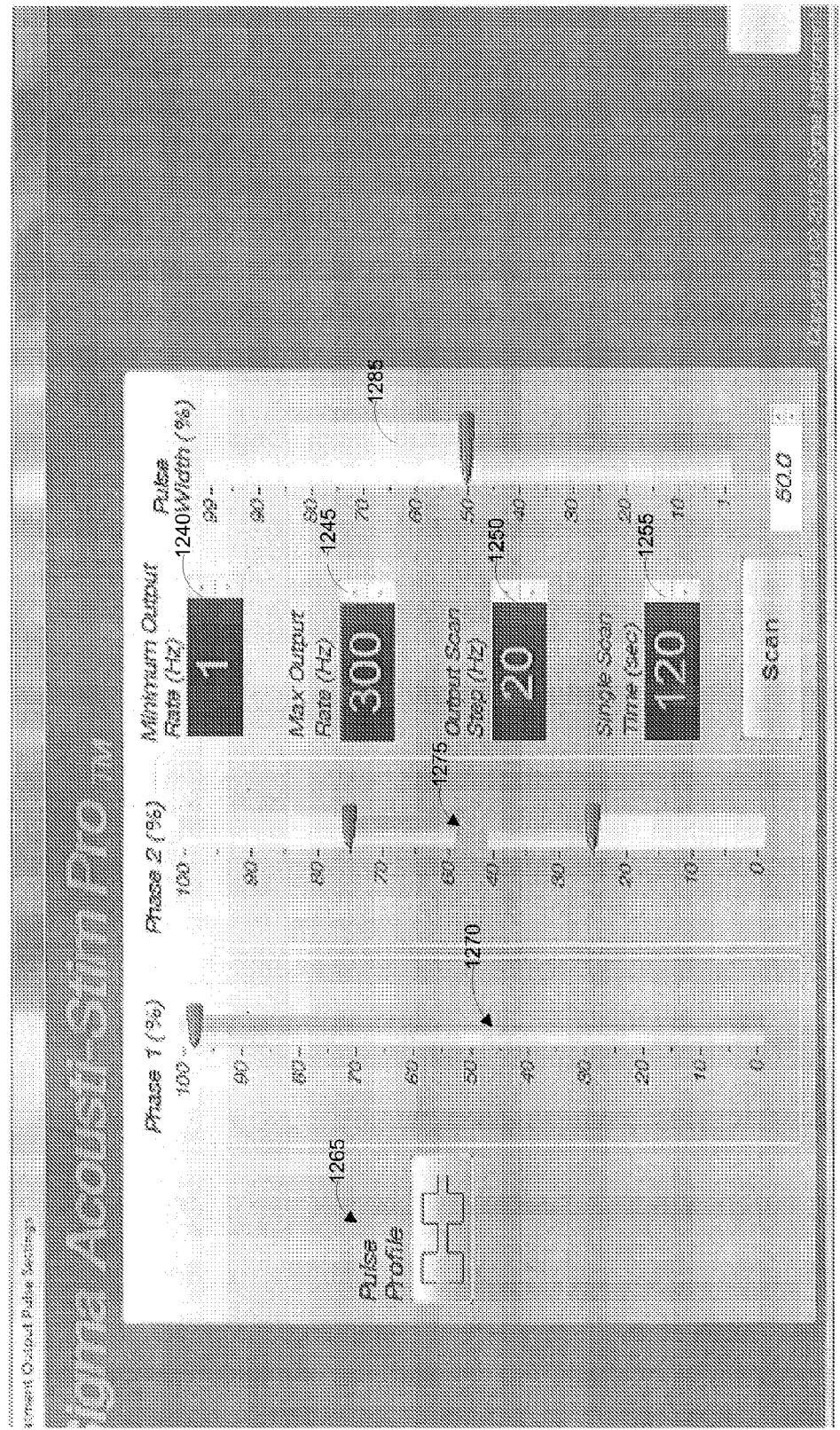

As the generator 315 causes the head 205b to sweep through the various frequencies, the EMG sensor 215 senses the resulting electromyogram in the patient. The comparitor 320, in conjunction with the CPU 40, identifies which pulse frequency of the range of pulse frequencies administered to the patient via the generator 315 and head 205b has the highest electromyogram reading in the patient. The system 10, via, for example, the display 30, recommends a treatment pulse frequency setting from the plurality of treatment pulse frequencies available to the treatment head 205b via the generator 315. For example, the EMG sensor and comparitor work together to determine a pulse frequency of 20 Hz resulted in the highest electromyogram readings in the patient. Accordingly, the system 10 recommends using the treatment RF head 205b to administer 600 KHz RF energy at a 20 Hz pulse frequency (i.e., the 600 KHz RF energy is pulsed at 20 Hz when being administered to the patient tissue). FIG. 10A illustrates a graph of RF energy being administered at the identified (optimum) RF frequency of 600 KHz 1200 and pulsed at the identified (optimum) pulse frequency of 20 Hz 1205, as used in this example. FIG. 10B is an example of a pulsed output signal similar to that depicted in FIG. 10A. FIG. 10C is an example of a modulated output signal. The signals original signals 1200 and 1205 may be modulated by varying the amplitude, phase, and/or frequency of the signals to arrive at the modulated signals 1210, 1215. In some embodiments of the system, the RF energy can be administered at an identified (optimum) RF frequency (e.g., 600 Hz) and pulsed at the identified (optimum) pulse frequency (e.g., 20 Hz) such that the RF energy is pulsed similar to that depicted in FIG. 10B. FIG. 10B-1 is a screen shot of the display 30 of the system 10 of FIG. 4, wherein the screen shot illustrates a manual pulse rate selection system for setting the parameters for a rectangle pulse output. As can be understood from FIG. 10B-1, the display 30 depicts the square pulse profile 1220, an output percentage setting 1225, a pulse rate setting 1230, and a pulse width setting 1235.

FIG. 10B-2 is a is a screen shot of the display 30 of the system 10 of FIG. 4, wherein the screen shot illustrates a scanned pulse rate selection system for setting the parameters for a rectangle pulse output. As can be understood from FIG. 10B-2, the display 30 depicts the square pulse profile 1220, an output percentage setting 1225, a minimum output rate setting 1240, a max output rate setting 1245, an output scan step setting 1250, a single scan time setting 1255, and a pulse width setting 1260.

In some embodiments, the RF energy at the identified RF frequency may be modulated at the identified pulse frequency similar to that depicted in FIG. 10C. FIG. 10C-1 is a screen shot of the display 30 of the system 10 of FIG. 4, wherein the screen shot illustrates a manual pulse rate selection system for setting the parameters for a modulated pulse output. As can be understood from FIG. 10C-1, the display 30 depicts the modulated pulse profile 1265, a phase 1 percentage setting 1270, a phase 2 percentage setting 1275, a pulse rate setting 1280, and a pulse width setting 1285.

FIG. 10C-2 is a is a screen shot of the display 30 of the system 10 of FIG. 4, wherein the screen shot illustrates a scanned pulse rate selection system for setting the parameters for a modulated pulse output. As can be understood from FIG. 10C-2, the display depicts the modulated pulse profile 1265, a phase 1 percentage setting 1270, a phase 2 percentage setting 1275, a minimum out put rate setting 1240, a max output rate setting 1245, an output scan step setting 1250, a single scan time setting 1255, and a pulse width setting 1285.

Figure 8:
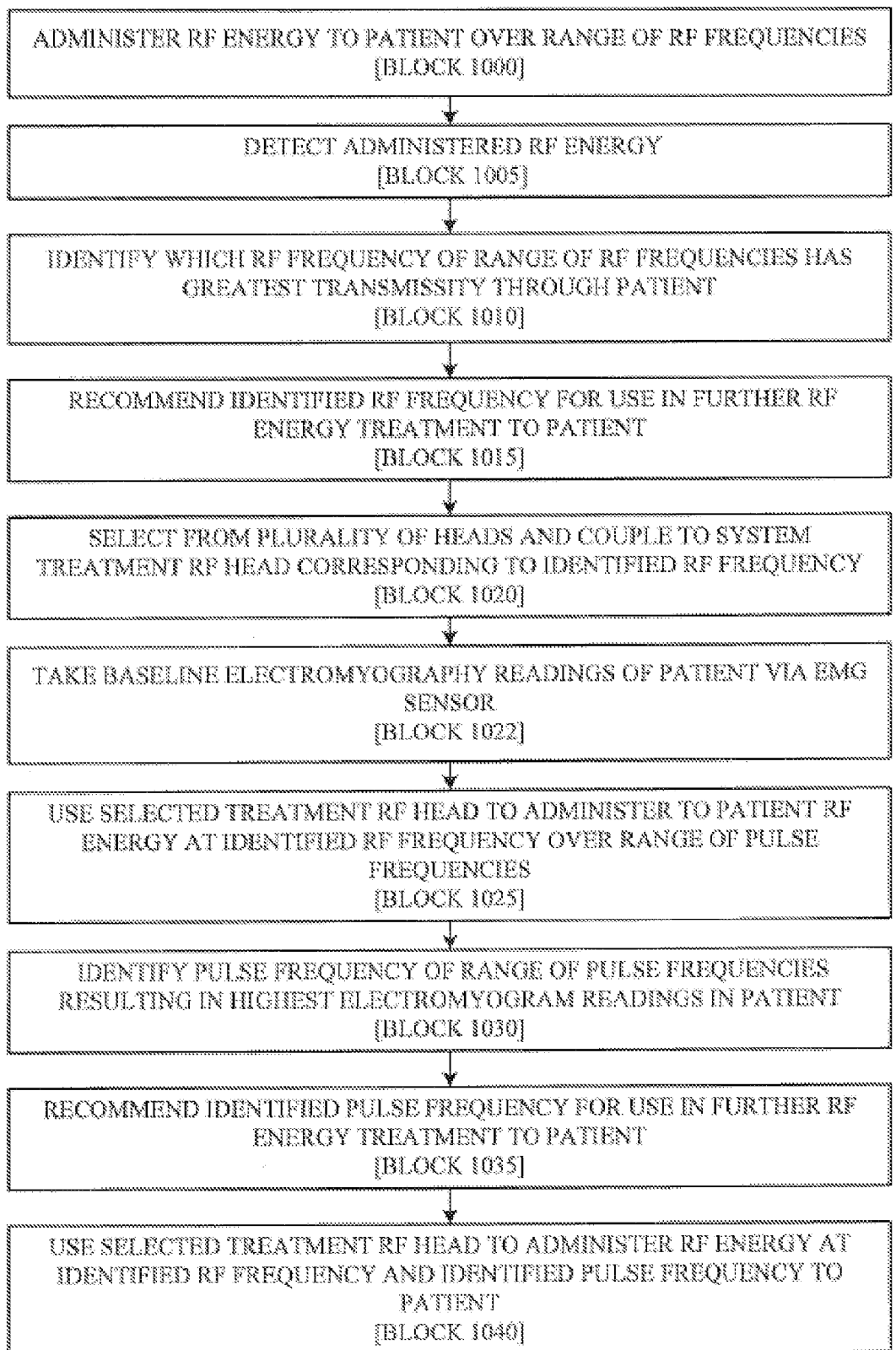
FIG. 8 is a flow chart illustrating an operational method associated with the system embodiment of FIG. 4.

As can be understood from the preceding discussion regarding FIGS. 4-7, a method is disclosed herein for preventing, managing and/or treating peripheral neuropathy and peripheral vascular disease in a patient wherein RF energy is applied to the patient tissue at a more transmissible RF frequency and at a pulse frequency that results in the highest electromyogram readings. For example, as can be understood from FIG. 8, via the transducer array 203 of the evaluation RF head 200, RF energy is administered to the patient over a range of RF frequencies [block 1000]. Via the RF receiver antenna and/or acoustic measuring device 210, the administered RF energy is detected [block 1005]. The CPU 40 and comparator 237 identifying which RF frequency of the range of RF frequencies has the greatest transmissibility through the patient [block 1010]. The display 30 recommends the identified RF frequency for use in further RF energy treatment to the patient [block 1015]. The applicable treatment RF head 205b corresponding to the identified RF frequency is selected from the plurality 202 of heads and coupled to the system 10 [block 1020]. Baseline electromyography readings are taken of the patient via the EMG sensor 215 [block 1022] followed by using the selected treatment RF head 205b to administer to the patient the RF energy at the identified RF frequency over a range of pulse frequencies [block 1025]. The EMG sensor 215, the comparitor 320 and CPU 40 are used to identify the pulse frequency of the range of pulse frequencies resulting in the highest electromyogram readings in the patient [block 1030], and the display 30 recommends the identified pulse frequency for use in further RF energy treatment to the patient [block 1035]. The selected treatment RF head 205b is then used to administer the RF energy at the identified RF frequency and identified pulse frequency to the patient [block 1040].

While the system embodiment discussed above with respect to FIGS. 4-8 applies to patient tissue RF energy at an identified RF frequency and identified pulse frequency, in some embodiments, the system 10 will apply an identified RF frequency over a range of stepped amplitudes instead of over a range of stepped pulse frequencies. Accordingly, one a specific stepped amplitude is identified as resulting in the highest EMG reading, the RF energy can be applied to the patient tissue at the identified RF frequency and identified amplitude.

By administering the RF energy to the patient tissue at an identified RF frequency and identified pulse frequency, the RF energy can be tailored to travel the greatest distance possible through the patient tissue at a pulse frequency that provides the greatest therapeutic result, as indicated by the EMG sensor readings, which give an instantaneous feedback of the therapeutic impact of the RF energy, such instantaneous feedback being less likely to be obtained via tissue temperature readings, tissue oxygenation readings, or other measurements. Over time and the course of treatment via the system 10, the patient tissue characteristics may change with respect to the RF frequency and/or the pulse frequency believed to be optimal for the therapeutic affect. Accordingly, the methodology outlined in FIG. 8 can be reapplied to identify a new optimal RF frequency, which will require the selection of a new treatment RF head from the plurality of such heads. Also, the new treatment RF head and above described methodology can be used to identify a new optimal pulse frequency. The system can then be used to administer the RF energy to the patient tissue at the new optimal RF and pulse frequencies.

Applying the pulsed RF energy to the patient tissue is advantageous in that it creates corresponding waves that travel through the patient tissue to release their energy at boundary layers such as, for example, facia, muscle, tendons or bone, etc. that are highly innervated. This release of mechanical energy at the boundary layers stimulates the nervous and vascular system, thereby providing a therapeutic benefit for preventing and/or treating peripheral vascular and peripheral neuropathy. Pulsing the RF energy at the optimal RF frequency also reduces tissue heating as compared to continuously applied RF energy at the optimal RF frequency.

Figure 9A:
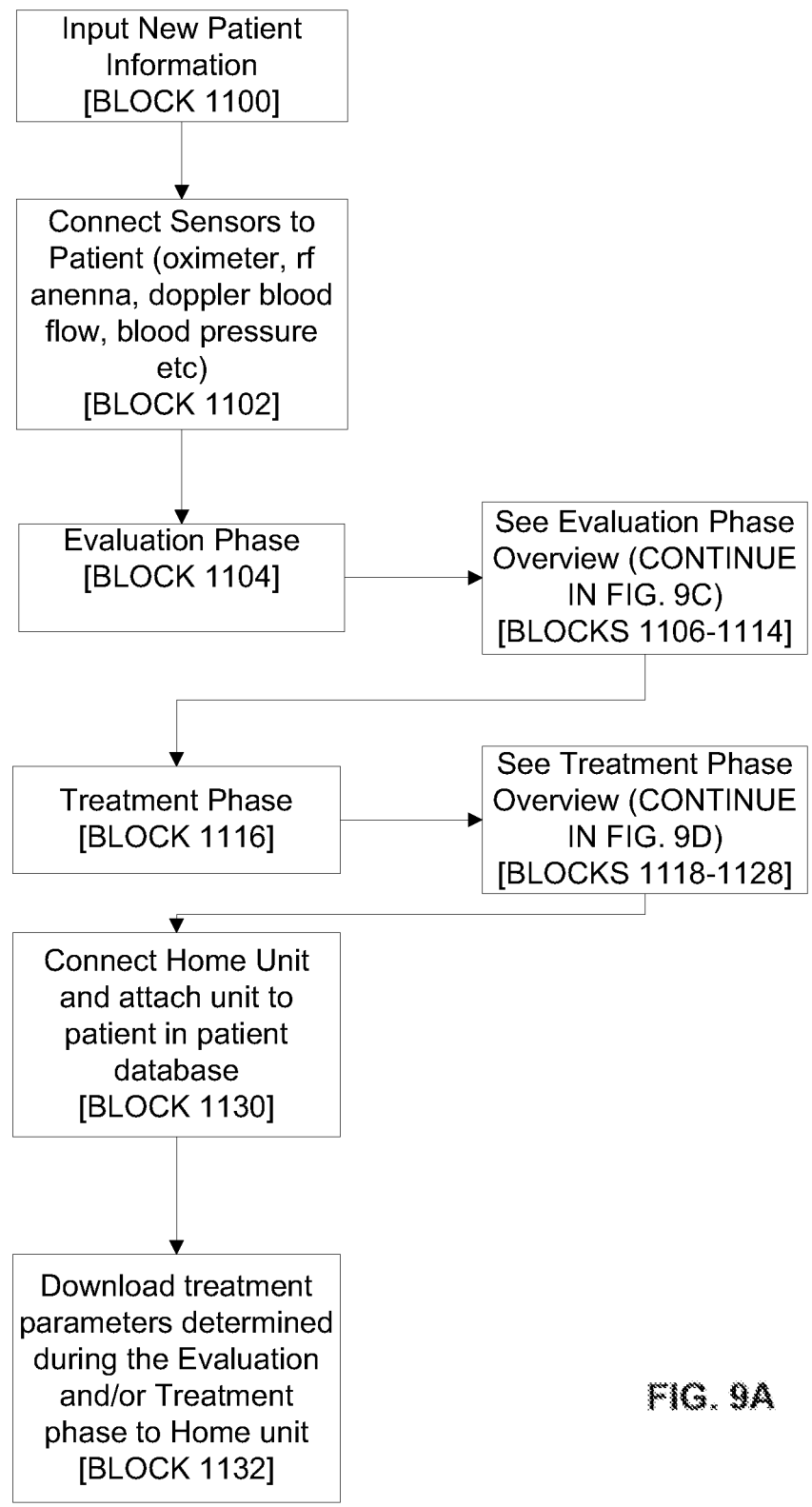
FIG. 9A is a flow chart illustrating a method of using the system embodiment of FIG. 4, wherein the system may include a clinical portion and a home-use portion.
Figure 9B:
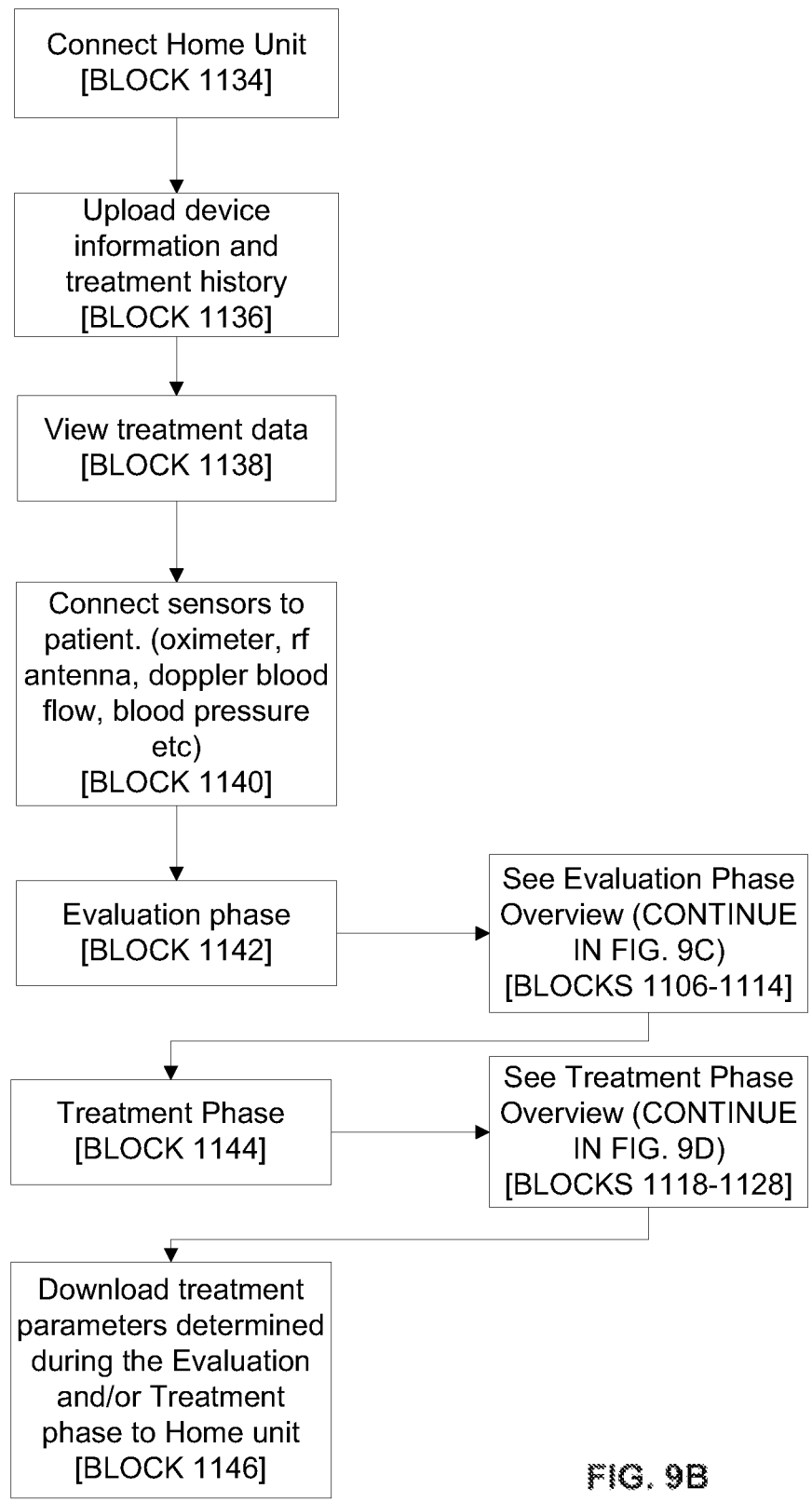
FIG. 9B is a flow chart illustrating a method of using the home-use portion of the system, wherein data and treatment information has been downloaded from the clinical portion into the home-use portion.
Figure 9C:
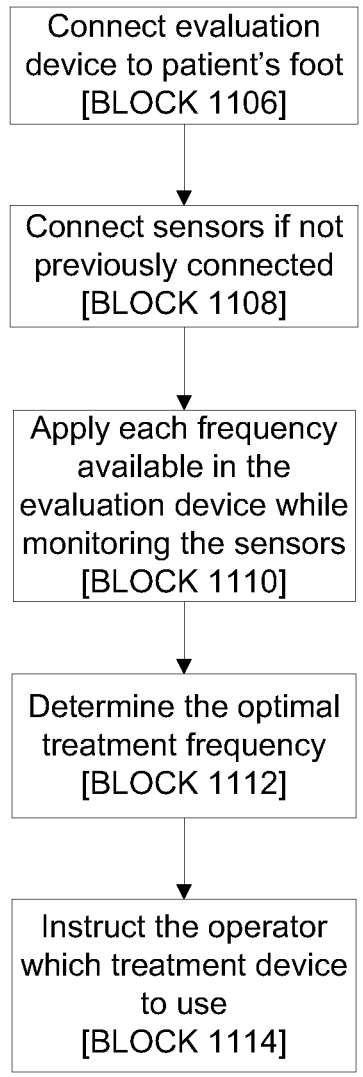
FIG. 9C is a flow chart illustrating an evaluation methodology employed with both the clinical and home-use portions.
Figure 9D:
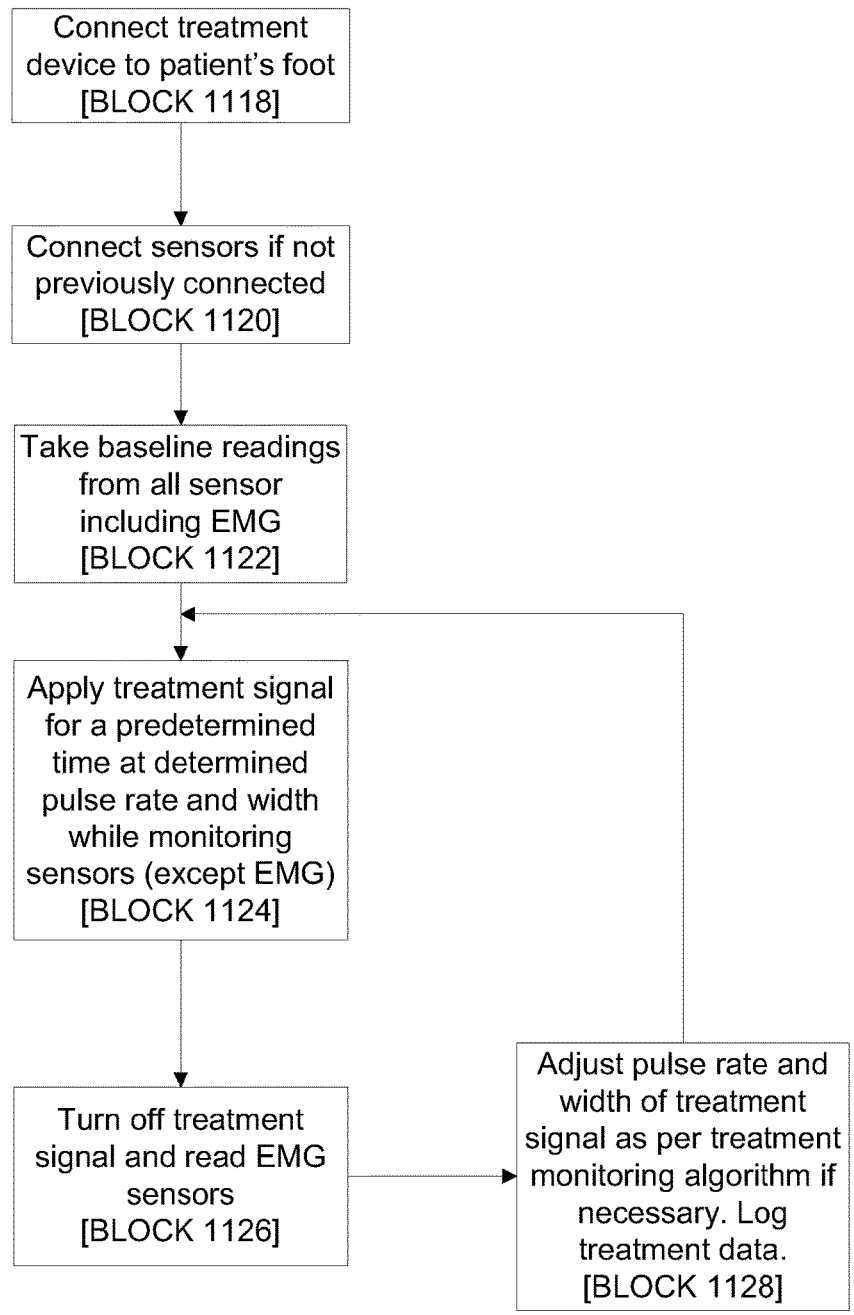
FIG. 9D is a flow chart illustrating a treatment methodology employed with both the clinical and home-use portions.

The system discussed with respect to FIGS. 4-8 can also be employed as depicted in the flow charts of FIGS. 9A-9D, wherein the system 10 may employ a clinical portion and a home-use portion. FIG. 9A is a flow chart illustrating a method of using the system embodiment of FIG. 4, wherein the system may include a clinical portion and a home-use portion. FIG. 9B is a flow chart illustrating a method of using the home-use portion of the system, wherein data and treatment information has been downloaded from the clinical portion into the home-use portion. FIG. 9C is a flow chart illustrating an evaluation methodology employed with both the clinical and home-use portions. FIG. 9D is a flow chart illustrating a treatment methodology employed with both the clinical and home-use portions. With respect to FIGS. 9A-9D, the clinical portion may be configured like the system 10 discussed above with respect to FIGS. 4-8, and the home-use portion may similarly configured but be in a more portable configuration, perhaps have fewer features as a result, and be capable of establishing a data link with the clinical portion.

Figure 9E:
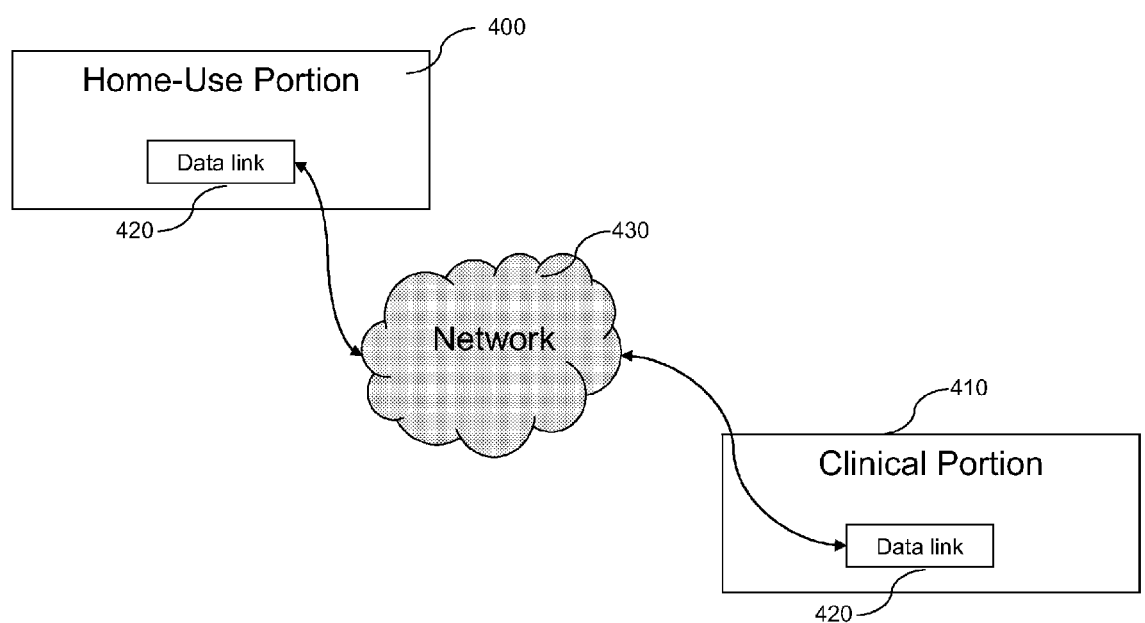
FIG. 9E is a schematic diagram of the system employing both the clinical and home-use portions connected by a network.
Figure 9F:
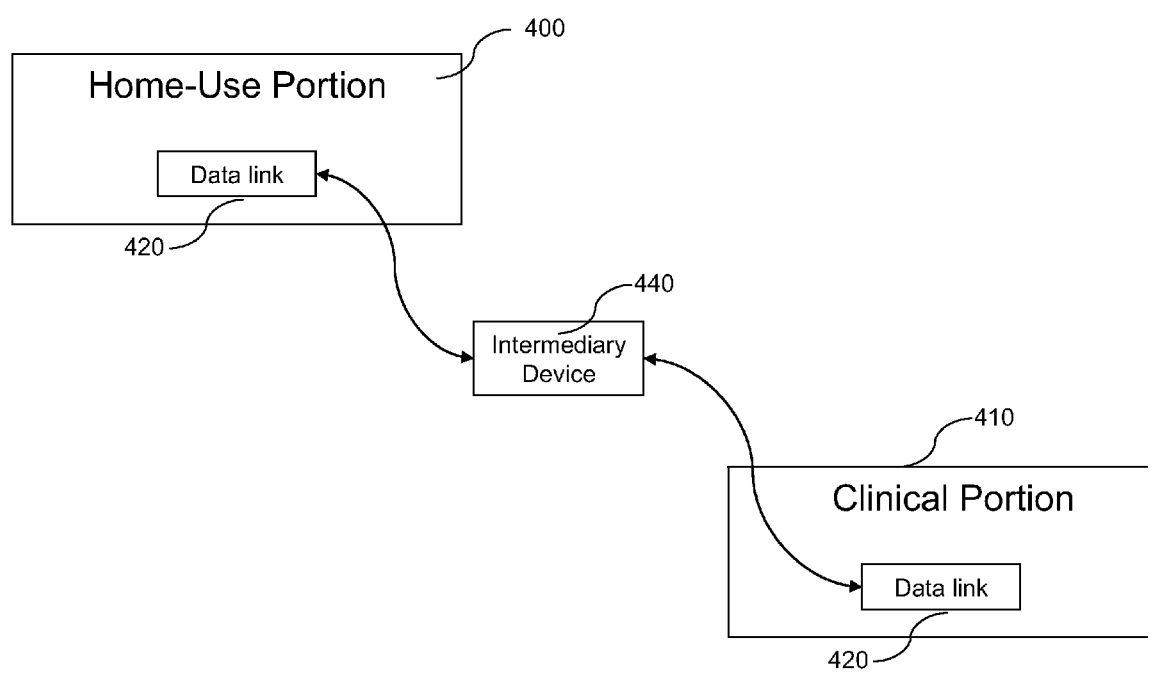
FIG. 9F is a schematic diagram of the system employing both the clinical and home-use portions connected by an intermediary device.

The system of FIGS. 9E-9F depict an embodiment of the system from FIGS. 4-8 which operates in accordance with FIGS. 9A-D. In this embodiment, the home-use portion 400 and the clinical portion 410 may connect via the data link 420. The data 420 link may comprise a connection between the home-use portion 400 and the clinical portion 410 capable of uploading data relating to the operation and/or results of the treatment carried out on the home-use portion 400. The data link 420 may comprise any means for connecting the home-use portion 400 to the clinical portion 410 or a server, file storage system, or database that is readable by the clinical portion 410. For example, as indicated in FIG. 9E the data link may comprise a network connection 430 such as an Ethernet or Wi-Fi connection, a cellular connection, or any other network connection, and may connect to the clinical portion 410 either directly or through an intermediary such as over the Internet or any other network. The data link 420 may then upload operation and/or results data to the clinical portion for analysis.

In various embodiments, the data link 420 may comprise an I/O port capable of capable of communicating with an intermediary device 440 that is communication with the clinical portion 410. For example, as illustrated in FIG. 9F the intermediary device 440 may comprise a portable data storage device capable of being physically transported to the clinical portion 410 or connected to a device in electrical communication with the clinical portion 410. This may include a universal serial bus (USB) port connected to a USB drive, such as a conventional USB flash drive, external hard drive, or other USB enable storage device. The USB drive may be connected to the home-use portion 400 and may receive data related to the operation and/or results of treatments carried out on the home-use portion 400 from the data link 420. The USB drive may then be physically taken to the location of clinical portion 410 and the data uploaded via the data link 420 onto the clinical portion 410. In various other embodiments, the USB drive may be connected to a home computer or any other Internet-enabled device and the data may be uploaded to the clinical portion 410.

In various embodiments, the data link 420 may be configured to automatically send the operation and/or results data to the clinical portion. This may be done every time the home use portion has completed treatment, at set time intervals, upon the request of the clinical portion, or according to the treatment results. For example, the data link may automatically upload the operations and/or results data at the end of every week. In another example, the data link may automatically upload the operations and/or results data when a result exceeds a threshold in some way. This may include one of many relevant comparisons. For example, besides tracking the user's treatment results, the home-use portion also may keep track of average results and standard deviation. If a user's results are unsatisfactory on average for a period of time, then modifications may be needed and the user's treatment and the data link may automatically send the operation and/or results data to the clinical portion regarding the poor results average. Similarly, if the user experiences outlier results that are outside of a set number of standard deviations from average, then the results may be uploaded. In the case of a non-network connected communications link, the user may be prompted by the home-use system to connect the intermediary device and either upload the data to the clinical portion or to take the intermediary device to their physician.

Figure 11:
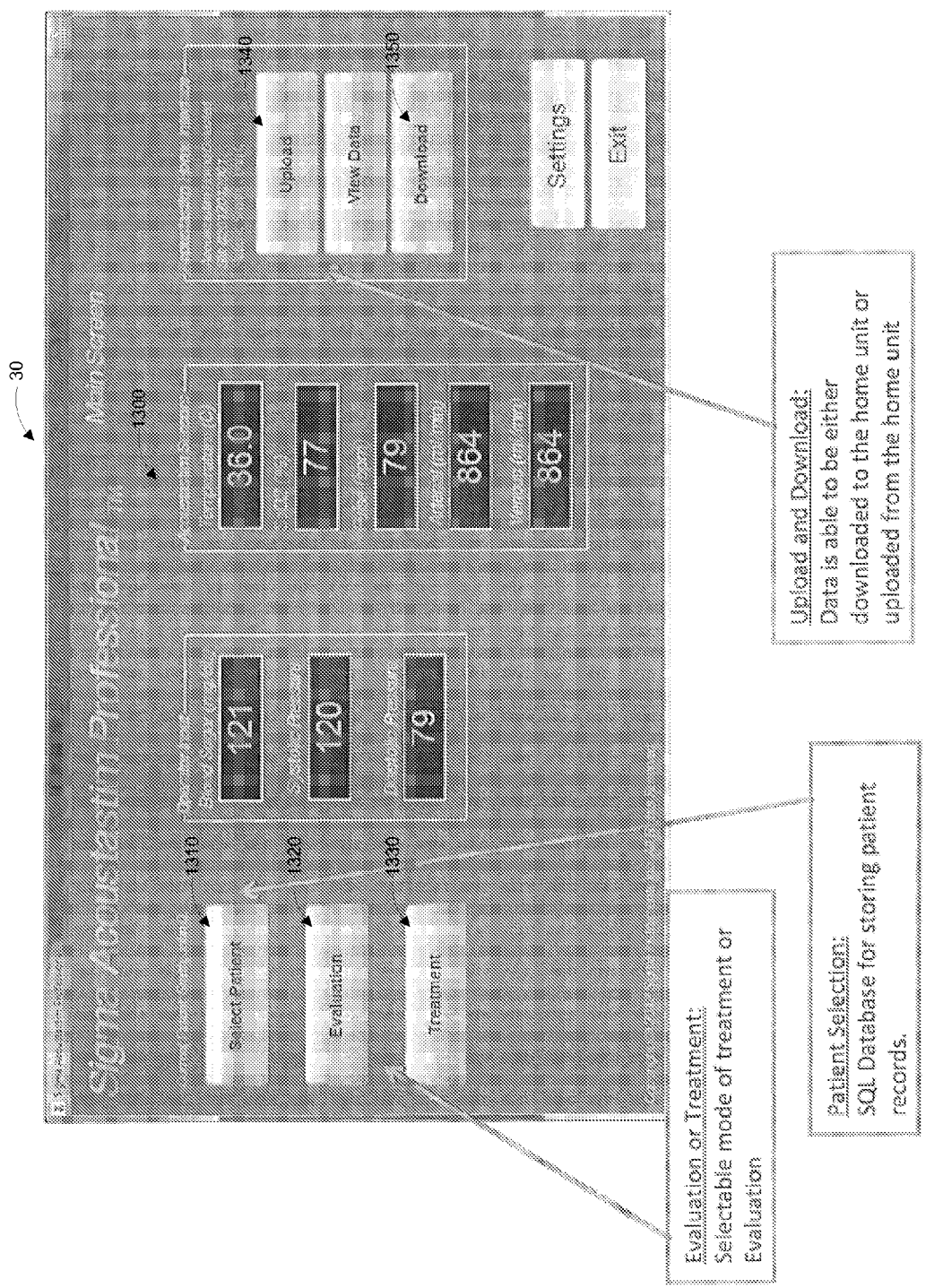
FIGS. 11-14 are screen shots of the display of the system, as described with respect to FIG. 4.

FIGS. 11-14 are screen shots of the display 30 of the system 10, as described with respect to FIG. 4. As shown in FIG. 11, which represents the home or main screen 1300, patient selection 1310 can be made from a database for storing patient records. Once the appropriate patient is selected from the database, the evaluation mode 1320 can be selected, followed by the treatment mode 1330. As described above, relevant treatment data can be uploaded 1340 from or downloaded 1350 to the home unit from the clinical unit via the communication links by selecting the appropriate button on the main screen 1300.

Figure 12:
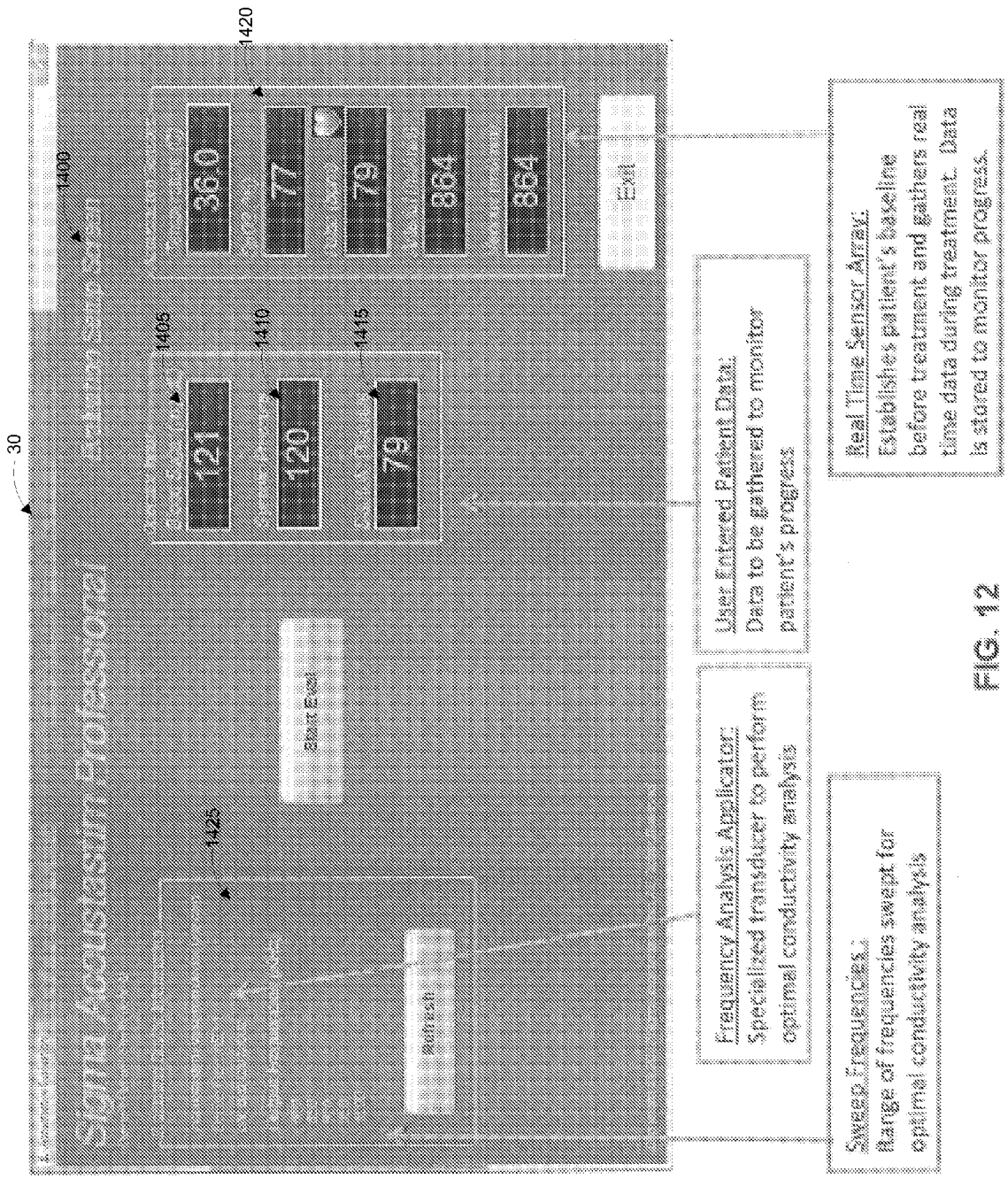

As indicated in FIG. 12, which represents the evaluation setup screen 1400, patient data such as blood sugar 1405, systolic pressure 1410 and diastolic pressure 1415 can be entered to monitor the patient's progress. A real time sensor array 1420 establishes the patient's baseline before treatment and gathers real time data during treatment, and this data is stored to monitor patient progress. A range of frequencies 1425 are swept for optimal conductivity (transmissibility) analysis, and the conductivity analysis uses the special transducer, namely the above describe transducer array, to perform the optimal conductivity analysis.

Figure 13:
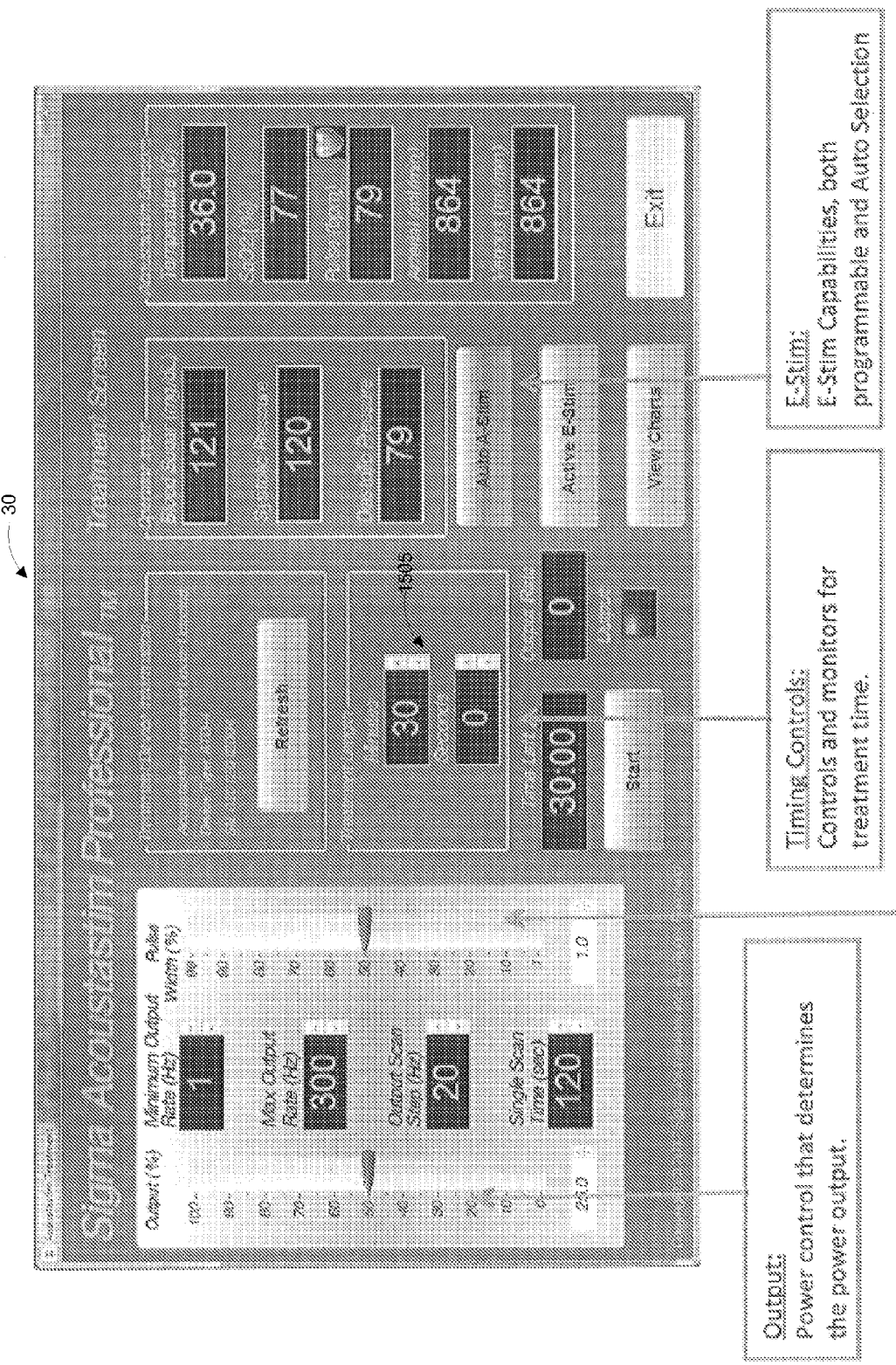

As depicted in FIG. 13, which represents the treatment screen, the power control determines the power output, and the pulse width controls the output pulse width. Timing controls 1505 and monitors for treatment time are provided. Also, the Estim capabilities are capable of being programmable or automatically applied.

Figure 14:
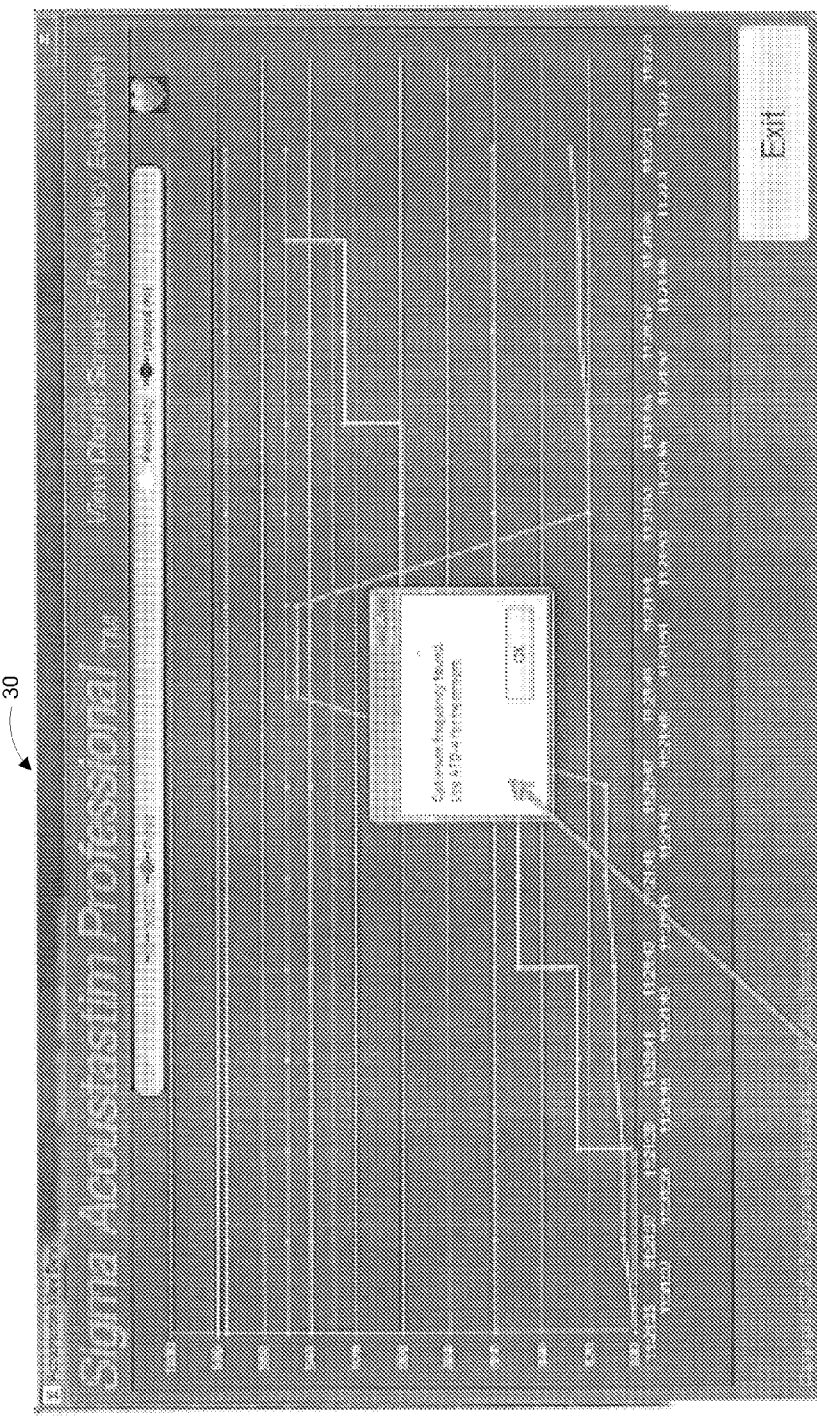

As illustrated in FIG. 14, which is a chart display of the frequency evaluation, a frequency evaluation graph can be displayed. Specifically, during the evaluation phase, the optimal frequency is detected and the appropriate transducer head is selected.

As can be understood from the preceding discussion regarding FIGS. 4-10, and with specific reference to FIGS. 9A-9D, the system 10 for measuring tissue response includes a transducer array capable of generating multiple frequencies within in the range of approximately 500 KHz to approximately 1,500 KHz, the system being designed to sweep the frequency range and measure the signal attenuation at a distal point with a frequency detector (e.g., antenna). For example, the transducer array would be attached to the patient foot and the antenna would be attached to the upper leg, as shown in FIG. 4. The system uses a computer to sweep the frequencies and measure and record the response, comparing the strength of the signal being transmitted through the tissue. After the system completes it scan, the software will identify the treatment head that best conducts the signal and identify it to the user. The system will save this information as a part of the user's data in a computer database for use as establishing a baseline frequency and to track any changes to the frequency over the course of treatments. This information is also used to determine the specific transducer that is to be used on the home use unit.

Also, as can be understood from the preceding discussion regarding FIGS. 4-10, the system 10 can be used to establish a baseline and monitor in real time neurological response of a patient using a surface EMG protocol. For example, an EMG or multiple EMG sensors are added to the patient. A software program interfaced with the EMG sensor records and establishes baseline information. Treatment is then initiated on the patient by the transducer of the identified treatment RF head. The EMG sensor can not record valid information while treatment is being performed. The software contains a gating protocol that intermittently stops the treatment in order to perform a new measurement(s). The system will save this information as a part of the user's data in a computer database for use as establishing a baseline EMG response and to track any changes to the EMG over the course of treatments. The Software protocol provides additional analytical capabilities during treatment.

The pulsed low frequency treatment spans a range of frequencies. With the addition of the EMG measuring protocol it can measure the near real time EMG response to specific frequencies in the treatment phase. The system will save this information as a part of the user's data in a computer database for use as establishing a baseline pulsed frequency and to track any changes to the pulsed frequency over the course of treatments. The pulsed frequency response can also be downloaded to a unit for home use.

Figure 15:
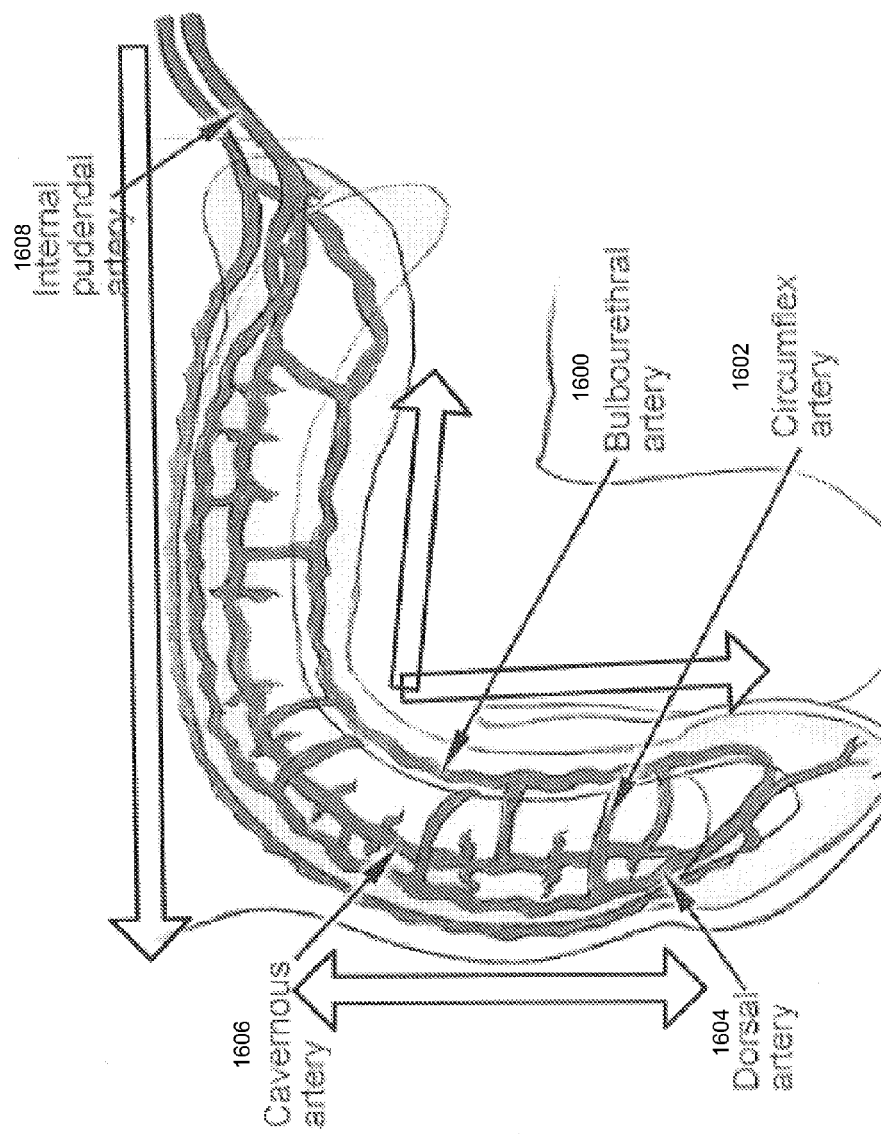
FIGS. 15-17 diagrammatical depictions of the artery, vein and nerve systems of the male reproductive system, respectively.
Figure 16:
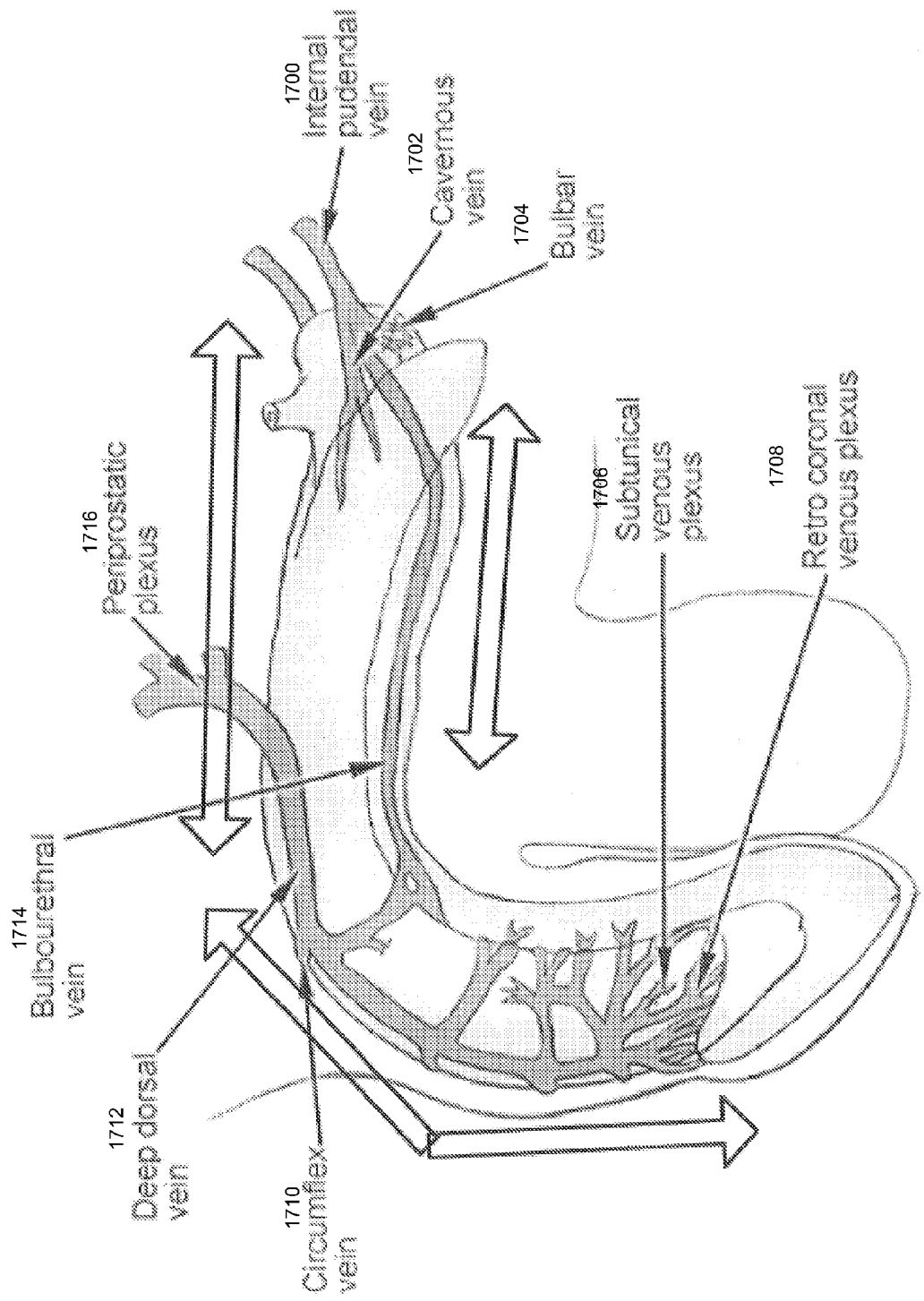
Figure 17:
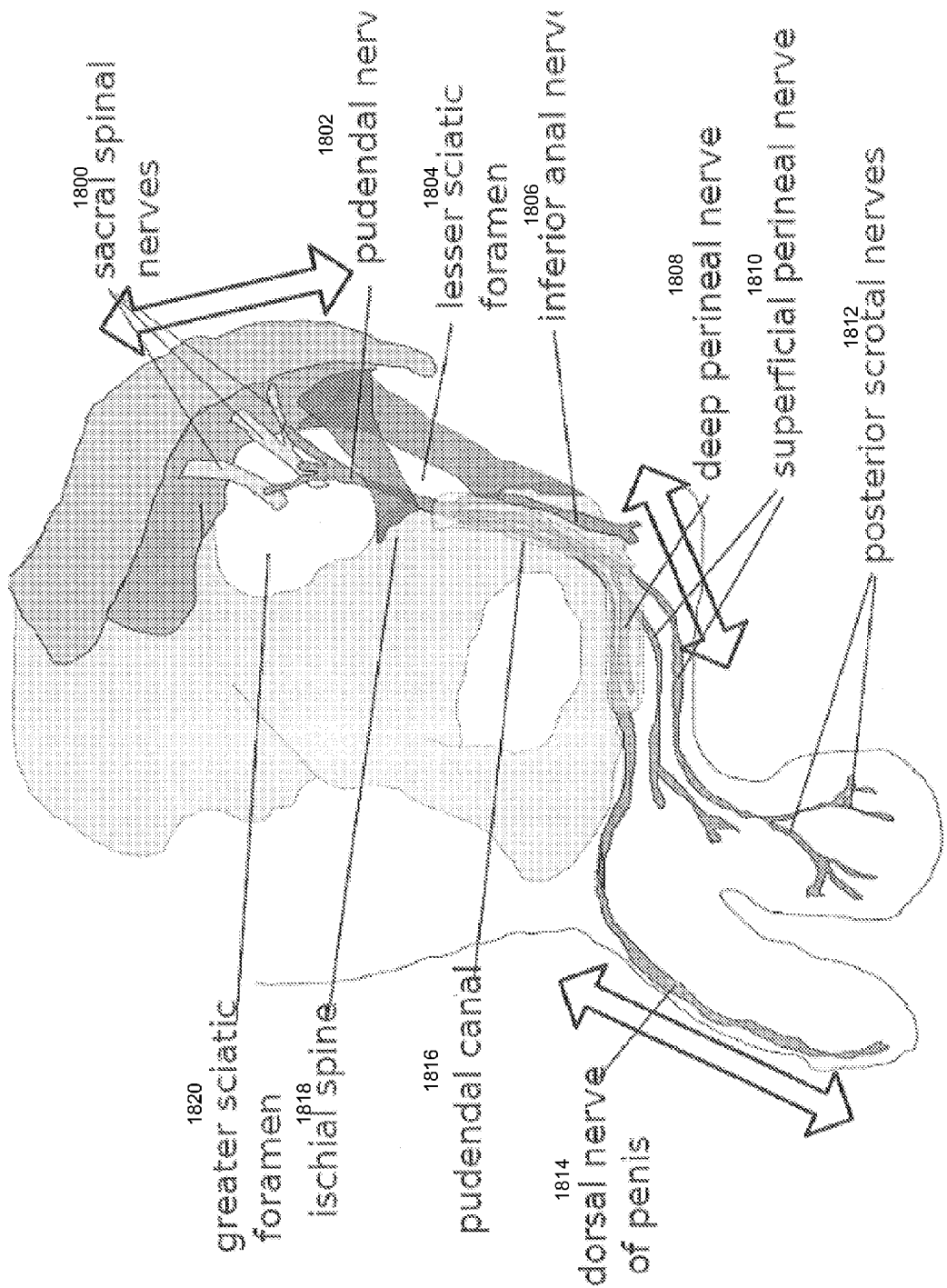

In some embodiments, the systems and methods described herein with respect to FIGS. 4-14 may be used to treat erectile dysfunction (ED) in male patients. FIGS. 15-17 are diagrammatical depictions of the artery 1600, 1602, 1604, 1606, 1608, vein 1700, 1702, 1704, 1706, 1708, 1710, 1712, 1714, 1716 and nerve systems 1800, 1802, 1804, 1806, 1808, 1810, 1812, 1814, 1816, 1818, 1820 of the male reproductive system, respectively. The arrows in each of FIGS. 15-17 illustrate treatment pathways along which the evaluation head 200 and the treatment head 205 are displaced in using the above-described system 10 to treat ED with the above-described methodology.

The male sexual response cycle consists of excitement, plateau, orgasm, and resolution. The initial event, penile erection, is produced by arteriolar dilatation and increased blood flow to the erectile tissue of the penis.

The innervation of the penis is both autonomic (i.e., sympathetic and parasympathetic) and somatic (i.e., sensory and motor). From the neurons in the spinal cord and peripheral ganglia, the sympathetic and parasympathetic nerves merge to form the cavernous nerves, which enter the corpora cavernosa and corpus spongiosum to affect the neurovascular events during erection and detumescence. The somatic nerves are primarily responsible for sensation and the contraction of the bulbocavernosus and ischiocavernosus muscles.

Penile erection is a vascular event in response to a reflex response initiated by visual, olfactory, or imaginative stimuli impinging upon supraspinal centers or by genital stimulation that in turn activates spinal reflex mechanisms. Sacral parasympathetic and thoracolumbar sympathetic nerves provide the efferent vasodilator input to the penis. Parasympathetic nerves also stimulate secretion from the seminal vesicles and prostate and Cowper's glands during the plateau phase. The orgasmic phase is characterized by seminal emission and ejaculation and the accompanying sensations. Emission of semen into the urethra depends on sympathetic nerves that elicit contractions of smooth muscles in the vas deferens, seminal vesicles, and prostate. Rhythmic contractions of striated muscle (i.e., bulbocavernosus and ischiocavernosus) generated by efferent pathways in the pudendal nerve eject semen from the urethra.

The spinal cord contains the autonomic preganglionic neurons that innervate the penile erectile tissue and the pudendal motoneurons that innervate the perineal striated muscles. Sympathetic pathways are anti-erectile, sacral parasympathetic pathways are pro-erectile, and contraction of the perineal striated muscles upon activity of the pudendal nerves improves penile rigidity. Spinal neurons controlling erection are activated by information from peripheral and supraspinal origin. Both peripheral and supraspinal information is capable of either eliciting erection or modulating or inhibiting an erection already present. Sensory information from the genitals is a potent activator of pro-erectile spinal neurons and elicits reflexive erections. Some premotor neurons of the medulla, pons and diencephalon project directly onto spinal sympathetic, parasympathetic and pudendal motoneurons, which receives sensory information from the genitals. These spinal projecting pathways release a variety of neurotransmitters, including biogenic amines (i.e., serotonin, dopamine, noradrenaline, and adrenaline) and peptides that, through interactions with many receptor subtypes, exert complex effects on the spinal network that controls penile erection.

The cavernous nerves (i.e., autonomic), which travel postarterolaterally to the prostate, enter the corpora cavernosa and corpus spongiosum to regulate penile blood flow during erection and detumescence. The dorsal nerves (i.e., somatic), which are branches of the pudendal nerves, are primarily responsible for penile sensation. During erection, relaxation of the trabecular smooth muscle and vasodilatation of the arterioles results in a severalfold increase in blood flow, which expands the sinusoidal spaces to lengthen and enlarge the penis. The expansion of the sinusoids compresses the subtunical venular plexus against the tunica albuginea. In addition, stretching of the tunica compresses the emissary veins, thus reducing the outflow of blood to a minimum. In the flaccid state, inflow through the constricted and tortuous helicine arteries is minimal, and there is free outflow via the subtunical venular plexus.

The penis is innervated by somatic and autonomic nerve fibers. The somatic innervation supplies the penis with sensory fibers and supplies the perineal skeletal muscles with motor fibers. Contraction of the perineal skeletal muscles during erection leads to a temporary increase in corporeal body pressure to a level above the mean systolic pressure, and thus helps to increase penile firmness.

The autonomic innervation of the penis is both parasympathetic and sympathetic. Stimulation of the pelvic plexus and the cavernous nerves induces erection, whereas stimulation of the sympathetic trunk causes detumescence. Thus, it is theorized that the sacral parasympathetic input is responsible for tumescence and the thoracolumbar sympathetic pathway is responsible for detumescence.

As can be understood from FIGS. 15-19, the major efferent parasympathetic pathway originates in the intermediolateral aspect of the sacral cord (S2-S4) 1905 traveling in the pelvic nerve 1910 (Nervi Erigentes) to supply a vasodilating innervation to the corporeal bodies. After the parasympathetic nerve fibers 1905 exit the spinal cord, they run through the retroperitoneal space in the lateral aspect of the rectum and bladder 1915, and then pass inferiorly and laterally toward the prostate 1920 and urogenital diaphragm. The cavernous nerve enters the corporeal body alongside the cavernous artery at the crura of the corpora as preganglionic nerve fibers. The most likely neurotransmitter at the synaptic end of these fibers is acetylcholine. The postganglionic nerve fiber segments terminate either on the vascular smooth muscle of the corporeal arterioles or the nonvascular smooth muscle of trabecular tissue surrounding the corporeal lacunae. The sacral parasympathetic neurons are chiefly responsible for the erectile function and are influenced by a cortical-sacral efferent pathway.

The penile erection can be initiated with a single episode of pelvic nerve electrical stimulation. Maintenance of erection for an extended period of time can be achieved with repetitive stimulation for 40-50 sec, with a minimum latency period of 50 sec between each stimulus. The sympathetic innervation of the penis mediates the detumescence after the orgasmic relief, and in the absence of sexual arousal it maintains the penis in the flaccid state.

In addition, depending on the intensity and nature of genital stimulation, several spinal reflexes can be elicited by stimulation of the genitalia, including the bulbocavernosus reflex. The somatic sensory innervation is important in the development and maintenance of normal erection, and the somatic motor innervation plays an important role in the control of ejaculation. While the above-described system 10 can be employed to treat erectile dysfunction, in some embodiments, the system 10 will be a portable hand-held version of the system 10 wherein the system employs a RF energy of a fixed frequency and variable amplitude.

In one embodiment, the RF pulses generated via the system 10 are administered to the patient so as to innervate the penile sensory afferent pathway as discussed above with respect to FIGS. 15-19. In one embodiment, the RF pulses generated via the system 10 are administered to the patient so as to innervate the Bulbocavernosus reflex (sacral reflex arc) by utilizing the dorsal penile/pudendal afferent pathway, the S2-S4 spinal cord segment, and the pudendal/perineal efferent pathway. In one embodiment, the innervation of the pudendal nerve somatosensory (i.e., genitocerebral) occurs via the peripheral and suprasacral afferent pathways by stimulating the pudendal nerve at the penis.

The cavernous nerve can be instrumental in producing an erection. Studies have show that stimulation of this nerve via implanted electrodes produces increased blood flow to the penis. However, this approach is invasive and requires surgery due to the location of the nerve. By using employing the systems 10 and methods disclosed herein, this nerve can be stimulated non-surgically.

In one embodiment of the systems 10 and methods disclosed above wherein said systems and methods are tailored for the treatment of erectile dysfunction, the system 10 applies RF energy at an identified (optimum) RF frequency to the tissues just under the prostate gland 1920, the RF frequency being pulsed at an identified (optimum) plus frequency within the range of between approximately 1 Hz to approximately 300 Hz to stimulate the cavernous nerve. In one embodiment, the RF frequency is pulsed within the range of between approximately 10 Hz to approximately 60 Hz to stimulate the cavernous nerve.

Figure 18:
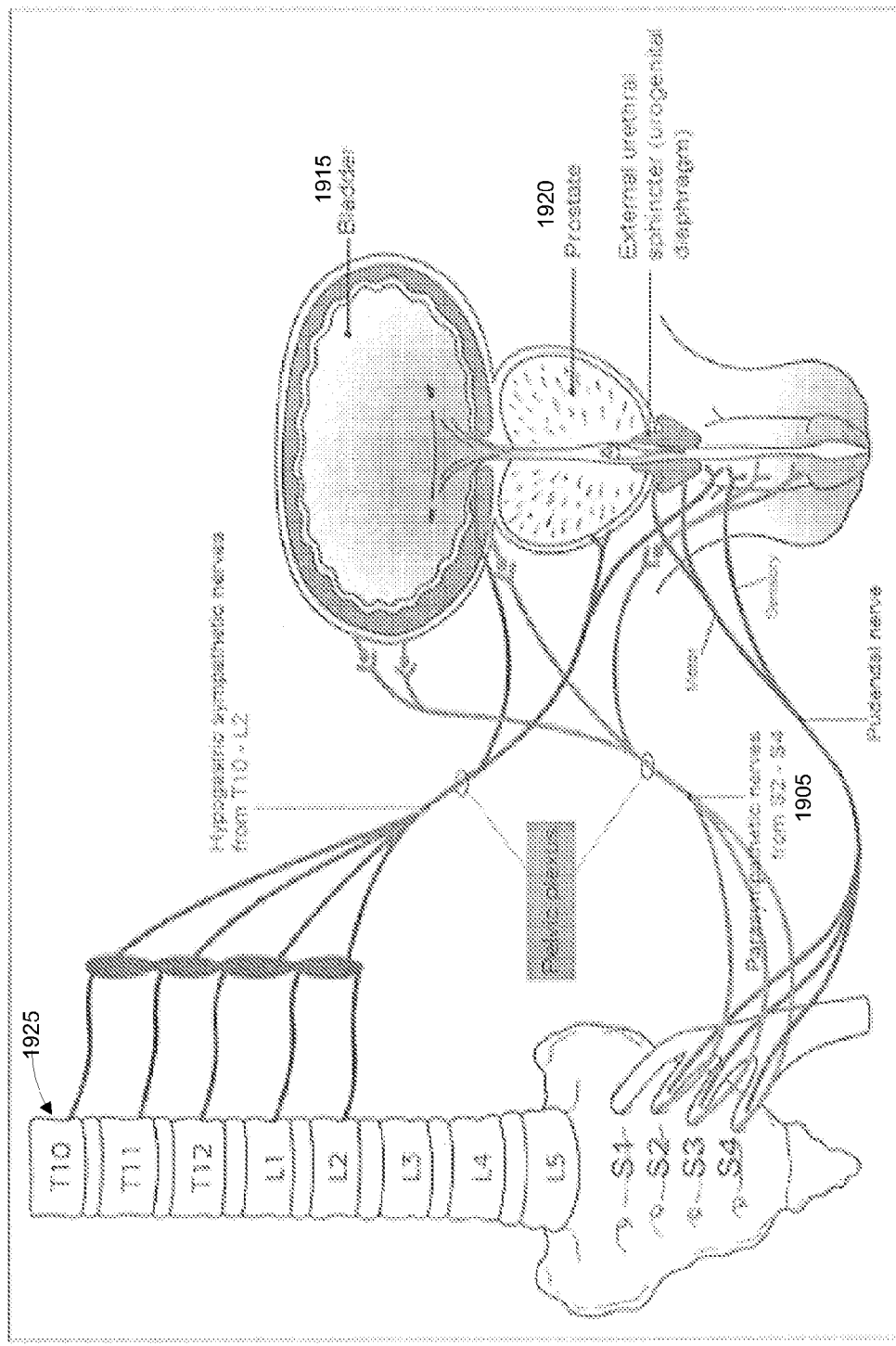
FIG. 18 is a diagrammatical depiction of the nervous system extending between the spine/sacrum complex to the bladder, prostate and penis.
Figure 19:
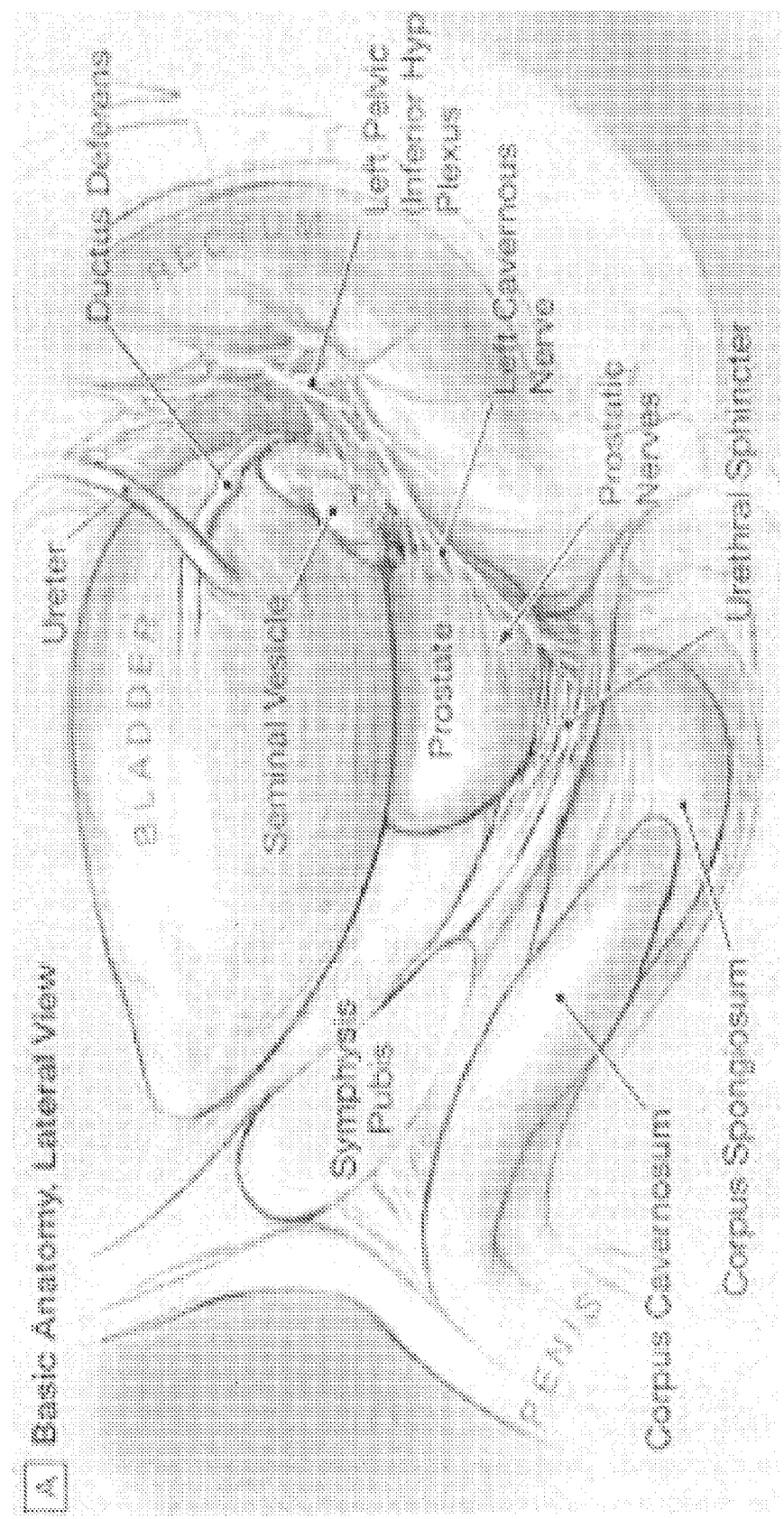
FIG. 19 is a lateral view illustration of the anatomical structures in the lower pelvic region.

As can be understood from FIGS. 18 and 19, in one embodiment, a the erectile dysfunction treatment methodology includes applying mechanical energy in the form of pulsed RF energy, percussive impulses, etc. to stimulate the parasympathetic 1900 where the nerve roots of the nerves exit the spinal column at T10, T11, L1, L2, S2, S3 and S4. The parasympathetic nerves 1900 that innervate the penis are depicted in FIG. 18, and these nerves will respond to applying mechanical energy in the form of pulsed RF energy, percussive impulses, etc.

In addition to or in place of applying the RF energy at the nerve roots of the nerves exiting the spinal column 1925 at T10, T11, L1, L2, S2, S3 and S4 to stimulate the parasympathetic, the application of the pulsed RF energy may be along the pathways indicated by the arrows in FIGS. 15-17 at frequency ranges of 1-30 Hz or 10-60 Hz.

In addition to being useful for the treatment of erectile dysfunction, the systems 10 and methods disclosed herein may be used for the treatment of urinary incontinence. For example, the system 10 can be used to stimulate nerve pathways via the application of pulsed RF energy to the nerve pathways, resulting in innervation of the pelvic plexus 1910 S2-S4 and the pudendal nerves 1930 via the peripheral and suprapubic afferent pathways. For example, the system 10 can be used to apply a pulsed RF energy to the tissues just under the prostate gland 1920 for male patients or the subrapubic area for female patients. The RF energy can be applied at an identified (optimum) RF frequency being pulsed at an identified (optimum) plus frequency within the ranges of approximately 1 Hz to approximately 300 Hz to stimulate the cavernous nerve. For example, in one embodiment of treating urinary incontinence, the system 10 can be used to administer the pulsed RF energy to stimulate the parasympathetic where the nerve roots of the nerves exit the spinal column at T10, T11, L1, L2, S2, S3 and S4.

By applying the pulsed RF energy as outlined above to treat the urinary incontinence, the RF energy can stimulate the nerves to address nerve issues and stimulate the sphincter muscle adjacent the urethra to tighten the sphincter and improve its effectiveness.

In one embodiment, the systems 10 and methods disclosed herein can be used to treat and reduce cellulite. Specifically, the pulsed RF energy can be applied to patient skin regions having cellulite, the pulsed RF energy smoothing the dimpled appearance of the cellulite.

Although the present invention has been described with reference to preferred embodiments, persons skilled in the art will recognize that changes may be made in form and detail without departing from the spirit and scope of the invention.

What is claimed is:
1. A method for treating peripheral neuropathy, peripheral vascular disease, erectile dysfunction, urinary incontinence, or cellulite in a patient, the method comprising:
    administering RF energy to the patient over a range of RF frequencies;
    detecting the administered RF energy with a RF antenna or an acoustic measuring device;

identifying, from the detection of the administered RF energy, which RF frequency of the range of RF frequencies has the greatest transmissibility through the patient;

recommending the identified RF frequency for use in further RF energy treatment to the patient;

administering the RF energy at the identified RF frequency to the patient over a range of pulse frequencies;

detecting electromyogram readings over the range of pulse frequencies with an EMG sensor;

identifying, from the detection of the electromyogram readings, which pulse frequency of the range of pulse frequencies results in the highest electromyogram readings in the patient;

recommending the identified pulse frequency for use in further RF energy treatment to the patient; and administering the RF energy at the identified RF frequency and identified pulse frequency to the patient.

2. The method of claim 1, wherein the administration of the RF energy to the patient over the range of frequencies is accomplished via a RF head having an array of piezoelectric transducers each tuned to an individual unique frequency, the array being configured to generate RF energy over a range of between 500 KHz and 1.5 MHz 1.5 MHz.

3. The method of claim 1, wherein the administration of the RF energy to the patient over the range of frequencies is over a range of between 500 KHz and 1.5 MHz at steps of between 50 KHz and 200 KHz.

4. The method of claim 1, wherein the recommending the identified RF frequency for use in further RF energy treatment to the patient includes identifying a specific RF head from a plurality of RF heads that is configured to provide the recommended RF frequency.

5. The method of claim 1, wherein the administering the RF energy at the identified RF frequency to the patient over a range of pulse frequencies occurs over a pulse frequencies ranging between 1 Hz and 300 Hz programmatically controlled and optimized for tissue type via stored protocols.

6. The method of claim 1, wherein the RF energy is administered to stimulate a parasympathetic where nerve roots of nerves exit a spinal column at T10, T11, L1, L2, S2, S3 and/or S4.

7. The method of claim 6, wherein the administering the RF energy at the identified RE frequency to the patient over a range of pulse frequencies occurs over a pulse frequencies ranging between 1 Hz and 300 Hz.

8. The method of claim 7, wherein the administration of the RF energy occurs in the context of treating erectile dysfunction.

9. The method of claim 8, wherein the RF energy is used to stimulate the cavernous nerve.

10. The method of claim 7, wherein the administration of the RF energy occurs in the context of treating urinary incontinence.

11. The method of claim 1, wherein the administration of the RF energy occurs in the context of treating cellulite.

* * * * *

UNITED STATES PATENT AND TRADEMARK OFFICE
CERTIFICATE OF CORRECTION

PATENT NO. : 9,861,547 B2
APPLICATION NO. : 14/344311
DATED : January 9, 2018
INVENTOR(S) : Crunick et al.

It is certified that error appears in the above-identified patent and that said Letters Patent is hereby corrected as shown below:

In the Claims

Claim 2, Column 19, Line 25, delete one of the occurrences of "1.5 MHz".

Claim 7, Column 20, Line 16, delete "RE" and replace with --RF--; Line 18, delete "300 Hz" and replace with --30Hz--.

Signed and Sealed this
Twenty-fourth Day of April, 2018

Andrei Iancu
*Director of the United States Patent and Trademark Office*